(12) United States Patent
Garnier

(10) Patent No.: US 6,201,086 B1
(45) Date of Patent: *Mar. 13, 2001

(54) ELECTRICALLY CONDUCTIVE ELECTROACTIVE FUNCTIONALIZED CONJUGATED POLYMERS, AND USES THEREOF

(75) Inventor: Francis Garnier, Champigny sur Marne (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/195,544

(22) Filed: Nov. 19, 1998

Related U.S. Application Data

(63) Continuation-in-part of application No. 08/564,246, filed as application No. PCT/FR95/00536 on Apr. 25, 1995.

(30) Foreign Application Priority Data

Apr. 22, 1994 (FR) ................................................. 94 05064

(51) Int. Cl.[7] ...................... C07D 207/00; C07D 295/00; C08F 26/06; C08F 126/06; C08F 226/06
(52) U.S. Cl. ............................................ 526/258; 548/518
(58) Field of Search .............................. 525/54.1, 54.11; 548/518; 526/258

(56) References Cited

U.S. PATENT DOCUMENTS 5,149,826 * 9/1992 Delabouglise et al. .............. 548/518

FOREIGN PATENT DOCUMENTS

| 0 157 326 | * | 10/1985 | (EP) . |
| 0 314 009 | * | 5/1989 | (EP) . |
| 1 2 607 507 | * | 3/1988 | (FR) . |
| 2 656 868 | * | 7/1991 | (FR) . |
| WO 90/10655 | * | 9/1990 | (WO) . |
| WO 93/06237 | * | 4/1993 | (WO) . |

OTHER PUBLICATIONS

F. Garnier, "Functionalized Conducting Polymers—Towards Polymers Intelligent Materials", *Advanced Materials*, vol. 101, No. 4, pp. 529–533, (1989).*
A. Deronzier et al., "Functionalized Polypyrroles. New Molecular Materials for Electrocatalysis and Related Applications", *Acc. Chem. Res.*, vol. 22, pp. 249–255, (1989).*
J. Roncali, "Conjugated Poly(thiophenes): Synthesis, Functionalization, and Applications", *Chem. Rev.*, vol. 92, pp. 711–738, (1992).*
J. Roncali et al., "Electroactive Conducting Compoisites from Poly(3–methylthiophene) and Poly(methylmethacrylate)", *J. Chem. Soc., Chem. Commun.*, pp. 783–784, (1986).*
G. Tourillon et al., "Electrochemical Doping of Polythiophene in Aqueous Medium", *J. Electroanal Chem.*, vol. 161, pp. 407–414, (1984).*
D. Delabouglise et al., "Chiral Metals: Amino Acid–Substituted Conducting Polypyrroles", *Synthetic Metals*, vol. 39, pp. 117–120, (1990).*

P. Bäuerle et al., "Synthesis and Properties of Carboxy–Functionalized Poly(3–alkylthienylenes)", *Advanced Materials*, vol. 2, No. 10, pp. 490–494, (1990).*
I.M. Chaiken, "Molecular Interactions, Affinity Methods, and the Developing Synergism Between Affinity Chromatography and Biological Recognition", *Affinity Chromatography and Biological Recognition*, pp. 3–6 (1983).*
B.M. Dunn et al., "Application of Quantitative Affinity Chromatography to the Study of Protein–Ligand Interactions", *Affinity Chromatography and Biological Recognition*, pp. 93–102 (1983).*
S. Avrameas et al, "Immunoassays Based on Specific Bio–Recognition", *Affinity Chromatography and Biological Recognition*, pp. 363–373 (1983).*
J.M. Egly, "Nucleic–Acids and Related Compounds in Affinity Chromatography", *Affinity Chromatography and Biological Recognition*, pp. 447–453 (1983).*
W.J. Feast, "Synthesis of Conducting Polymers", *Handbook of Conducting Polymers*, vol. 1, pp. 1–44 (1986).*
A.F. Diaz et al., "Electrochemical Synthesis of Conducting Polymers", *Handbook of Conducting Polymers*, vol. 1, pp. 81–115 (1986).*
G.B. Street, "Polypyrrole from Powders to Plastics", *Handbook of Conducting Polymers*, vol. 1, pp. 265–291 (1986).*
G.A. Kossmehl, "Semiconducting and Conducting Polymers with Aromatic and Heteroaromatic Units" *Handbook of Conducting Polymers*, pp. 351–403 (1986).*
J.R. Ellis, "Commercial Applications of Intrinsically Conducting Polymers", *Handbook of Conducting Polymers*, vol. 1, pp. 489–499 (1986).*
J.M. Pochan, "The Oxidative Stability of Dopable Polyenes", *Handbook of Conducting Polymers*, vol. 1, pp. 1383–1405 (1986).*
M. Egholm et al., "Peptide Nucleic Acids (PNA) Oligonucleotide Analogues with an Achiral Peptide Backbone", *J. Am. Chem. Soc.*, vol. 114, pp. 1895–1897 (1992).*

(List continued on next page.)

*Primary Examiner*—Nathan M. Nutter
(74) *Attorney, Agent, or Firm*—Oliff & Berridge, PLC

(57) ABSTRACT

There are electrically conductive, electroactive functionalized conjugated polymers having formula (I):

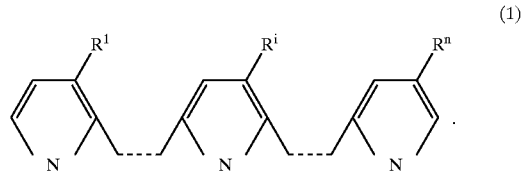

(1)

These electrically conducive, electroactive conjugated polymers may be covalently bonded to a first biological molecule or antiligand. Polymers bonded to a first biological molecule or antiligand may be used to form an electrode and may be used to assay for, detect and/or extract a second biological molecule or ligand.

29 Claims, 12 Drawing Sheets

OTHER PUBLICATIONS

J.R. Uren, "Affinity Chromatography of Proteolytic Enzymes", *Biochimica Et Biophysica Acta*, vol. 236, pp. 67–73 (1971).*

A. Dutta, "Design and Therapeutic Potential of Peptides", *Advances In Drug Research*, vol. 21, p. 145, (1991).*

* cited by examiner

Py A (1)

Py A (Gly-dPhe) (2)

Py A (Val) (3)

Py A (Phe)  (4)

Py A (Phe-Pro)
(5)

Py A (Phe (Hea) Pro)
(6)

ELECTRICALLY CONDUCTIVE ELECTROACTIVE FUNCTIONALIZED CONJUGATED POLYMERS, AND USES THEREOF

This is a Continuation-in-Part of application Ser. No. 08/564,246 filed Feb. 6, 1996, which in turn is a U.S. National Stage of PCT/FR95/00536 filed Apr. 25, 1995. The entire disclosure of the prior application is hereby incorporated by reference herein in its entirety.

Conjugated polymers, such as polypyrroles, polythiophenes, polyanilines, polyphenylenes and derivatives thereof are known for their electroactive nature, which is widely described in review works such as the "Handbook of Organic Conducting Polymers" (T. J. Skotheim Editor, Marcel Dekker, New York, 1986). These polymers are obtained in the form of a film on an electrode, in the form of self-supporting films or alternatively in the form of a composite when combined with a polycationic or polyanionic polymer and behave like organic electrodes, which charge up according to an anodic oxidation process, by insertion of ions from the electrolytic medium. This electrochemical process is reversible, the reduction leading to the expulsion of the ions from this conjugated polymer or from the electroactive composite.

A second generation of conjugated polymers was then described in the literature, obtained by the covalent grafting, on to the monomer units of the polymers, of functional groups capable of providing these electroactive conjugated polymers with an additional function. By way of example, electrocatalytic metal complexes were grafted on to the monomer units of the polypyrrole, specific complexing macrocycles were grafted on to the polypyrrole or polythiophene chains for the recognition of cations in an electrolytic medium, and chiral groups were grafted on to polythiophenes for the recognition of optically active anions. All of these routes of functionalization have also formed the subject of development procedures detailed in the literature (F. Garnier, Angew. Chemie, 1989, 101, 529; A. Deronzier, J. C. Moutet, Acc. Chem. Res. 1989, 22, 249; J. Roncali, Chem Rev., 1992, 92, 711).

In the last few years authors have become interested in the use of functionalized conductive polymers for the development of analyte scavengers, in particular for diagnostic purposes. However, as indicated in patent application EP0 314,009, it was commonly accepted by the scientific community that pyrrole polymers substituted either on the nitrogen atom or directly on the carbon atoms of the pyrrole ring were not good candidates for the development of analyte scavengers, in particular on account of the loss of conductivity of said polymers when functional groups are introduced on to the heteroatomic ring. In order to overcome this problem, the authors of this patent application thus envisaged the use of 2,5-di(2-thienylpyrrole) polymers which were grafted in the 3-position of the pyrrole ring with a reactive moiety with which an organic molecule could become covalently bonded. It should, however, be noted that on account of the hydrophobicity of the thiophene rings, the polymers described cannot be conductive and electroactive in aqueous media and consequently do not appear to be suitable for the detection and/or characterization of an analyte in a biological sample (see J. Roncali et al., Chem. Comm., 1986, page 783 and G. Tourillon et al., Electronal. Chem., 161, 407, 1984).

It has now been discovered, entirely surprisingly and contrary to what was hitherto accepted by specialists, that the conductivity and electroactivity of polypyrroles are retained provided that a functional group is grafted in the 3- or 4-position on the pyrrole ring using a functionalizing agent which allows the intended function to be distanced from the pyrrole ring. An antiligand is covalently bonded to the free end of the functional group, without the abovementioned properties of the polymer being modified. Such functionalized polymers have to date never been described and have shown themselves to be entirely suitable as scavengers for a biological ligand. Moreover, polypyrroles prove to be advantageous polymers on account of their biocompatibility. Lastly, the polypyrroles thus functionalized make it possible to prepare electroactive and conductive polymers of considerable thickness (up to several millimeters thick), which thereby allows a great density of functional sites and proportionately improves the sensitivity.

The subject of the invention is thus an electrically conductive electroactive functionalized polymer which corresponds to the formula (I):

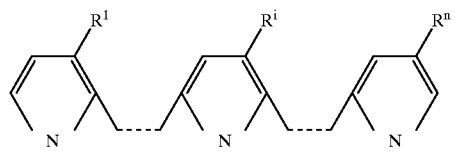

in which:

n is a non-zero integer and i is an integer ranging from 2 to n−1, and

R1, Ri and Rn, which may be identical or different, each represent H or a functional group capable of covalently bonding with a first biological molecule or antiligand, and in that said polymer has a conductivity and an electroactivity which are substantially of the same order as that of the corresponding non-functionalized conjugated polymer, that is to say of the corresponding polymer of formula I, in which R1, Ri and Rn each represent H.

More particularly, the functional group(s) is(are) independently chosen from the following set of functional groups:

$Y_p$—C—X where X represents H, OH, a substituted or unsubstituted lower O-alkyl radical, or a halogen, in particular Cl; Yp—NHZ, Z representing H or an alkyl radical; $Y_p$—NH—CO—CF$_3$; $Y_p$—X where X corresponds to the above definition, p being an integer preferably equal to 0, 1 or 2; —Si(alkyl)$_3$, —Si(alkoxyl)$_3$ or an activated ester group such as COON-hydroxysuccinimide.

Y preferably represents a group chosen from alkyls having from 1 to 5 carbon atoms, alkoxyls having from 1 to 5 carbon atoms and polyethers corresponding to the general formula (CH2—CH2—O)m—(CH2)m'—, m representing an integer ranging from 1 to 3 and m' an integer equal to 1 or 2.

The invention also concerns an electrically conductive, electroactive functionalized conjugated polymer of formula (I')

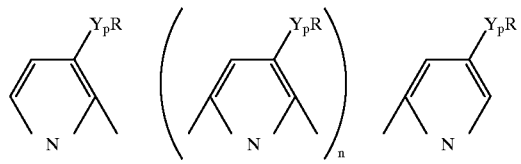

wherein n is an integer or zero, each R, which may be identical or different from one monomer unit to one another, is selected from the group consisting of H and functional groups capable of covalently bonding with a first biological molecule or antiligand with the proviso that (a) at least one said R of formula (I') represents said functional group or (b) is each $Y_pR$ in formula (I') is identical, they are different from $CH_2$—COOH, each $Y_p$, which may be identical or different from one monomer unit to one another, is a coupling arm wherein p is zero or an integer, wherein said polymer has a conductivity and an electroactivity which are substantially of the same order as a conductivity and an electroactivity of a corresponding polymer of formula (III), in which each said R represents H.

Preferably, p is 0, 1 or 2

Preferred polymers of formula (I') are the following:

polymers wherein R is selected from the group consisting of COX, where X represents H, OH, a substituted or unsubstituted lower O-alkyl radical or an halogen; activated esters; NHZ where Z represents H, an alkyl radical or CO—$CF_3$; Si(alkyl)$_3$; Si(alkoxyl)$_3$; electrochemical probes; electrochemical probes bound to an activated ester; electrochemical probes are preferably selected from the group consisting of ferrocene and quinone and/or activated esters are selected from the group consisting of COON-hydroxysuccinimide, COON-hydroxyphtalimide, and COO-pentafluorophenol; the halogen is preferably chlorine;

polymers wherein p is at least one and R is selected from the group consisting of H, OH, a substituted lower O-alkyl radical, and a halogen;

polymers wherein Y is selected from the group consisting of alkylene groups having from 1 to 5 carbon atoms; oxy-alkylene groups having from 1 to 5 carbon atoms; polyethers having the formula [$(CH_2$—$CH_2$—$O)_m(CH_2)_{m'}$] where m is an integer ranging from 1 to 3 and m' is an integer equal to 1 or 2; $(CH_2)_mCONH(CH_2)_{m''}$ where each of m and m'' identical or different is an integer ranging from 1 to 3; $(CH_2)_mCON(CH_2)_{m'''}$ where m is an integer ranging from 1 to 3 and m''' is 2 or 3;

Said antiligand is able to form an antiligand/target molecule complex. Preferably, said complex is selected from the group consisting of peptide/antibody, antibody/haptene, hormone/receptor, polynucleotide hybrids/polynucleotide and polynucleotide/nucleic acid couple.

The target molecule may comprise a histidine tag.

More preferred polymers are the following:

polymers (A) wherein p is 1, Y is selected from the group consisting of $CH_2$, $CH_2$—$CH_2$ and $CH_2$—$CH_2$—$CH_2$, and at least one said R is COOH; this substituent $Y_pR$ is able to show a reactivity toward amino functions of a biological probe (for example, oligonucleotide, oligonucleotide derivatized with an amino function, amino acid, peptide), allowing the further grafting of this biological probe on the homo- or co-polymer; such substituent is also very useful for increasing the hydrophilicity of the homo- or co-polymer, while it is essential for the electrochemical behavior in aqueous solution;

polymers (B) wherein p is 1, Y is selected from the group consisting of $CH_2$, $CH_2$—$CH_2$ and $CH_2$—$CH_2$—$CH_2$, and at least one said R is an activated ester; a preferred activated ester is selected from the group consisting of COON-hydroxysuccinimide, COON-hydroxyphtalimide, and COO-pentafluorophenol; this substituent $Y_pR$ has a high reactivity with amino functions of amino acids or peptides for example, allowing the further grafting of such a biological probe on the homo- or co-polymer;

polymers (C) wherein p is 1, Y is $(CH_2)_mCONH(CH_2)_{m''}$ where each of m and m'' identical or different is an integer ranging from 1 to 3, and at least one said R is an electrochemical probe; a preferred electrochemical probe is selected from the group consisting of ferrocene and quinone; the electrochemical probe is selected for its sharp electrochemical signal, which improves the electrochemical detection sensitivity of the biological sensor;

polymers (D) wherein p is 1, Y is $(CH_2)_mCONH(CH_2)_{m''}$ where each of m and m'' identical or different is an integer ranging from 1 to 3, and at least one said R is an electrochemical probe bound to an activated ester; preferred electrochemical probes and preferred activated esters are as set forth above; the objective of this substituent $Y_pR$ is to allow, through the activated ester, the further grafting of a biological probe;

polymers (E) wherein p is 1, Y is $(CH_2)_mCONH(CH_2)_{m''}$ where each of m and m'' identical or different is an integer ranging from 1 to 3, and at least one said R is $NH_2$ or any substituent possessing a terminal amino function $NH_2$; the amino function is dedicated to the further grafting of a biological probe through an acidic function (COOH or $P(OH)_n$) present in the biological probe (for example, amino acid, peptide, oligonucleotide, antigen);

polymers (F) wherein p is 1, Y is $(CH_2)_mCON(CH_2)_{m'''}$ where m is an integer ranging from 1 to 3 and m''' is 2 or 3, and at least one said R is COOH; this substituent $Y_pR$ having the formula $(CH_2)_mCON(CH_2COOH)_{m'''}$ can complex transition metal ions (Ni, Co, Fe, Cu, . . . ) on which a further complexation of biological probe is possible, owing to the complexing properties of these transition metal ions with some derivatives such as histidine; for instance, a histidine tag can be grafted on a biological probe, allowing the probe to be complexed to the metal ion, and thus anchored to the functionalized poly(pyrrole).

Those preferred mono- or co-polymers may be obtained by electropolymerization of the corresponding monomer units, in various solvents such as acetonitrile or propylene carbonate, in presence of an electrolyte such as $LiClO_4$, with a concentration of about 0.1 M/l, at a constant potential of about 0.9 V/SCE, or a constant current density of some $mA/cm^2$, or by cyclic voltammetry. Typical concentration of monomer units is ranging from $10^{-2}$ to $10^{-1}$ M/l. They can be polymerized alone leading to homopolymers. Mixtures of monomers will result in co-polymers, in which one can associate various properties; for instance, a copolymer of poly (A, B, C) allows to associate the hydrophilic property of A, required for a sensing in aqueous solution, with the sharp signal of the electrochemical probe C together with the recognition property exerted by the biological probe of B with the biological target in solution.

Another subject of the invention is an electrically conductive electroactive conjugated polymer comprising at least one functional group which is covalently bonded to a first biological molecule or antiligand corresponding to the formula (II):

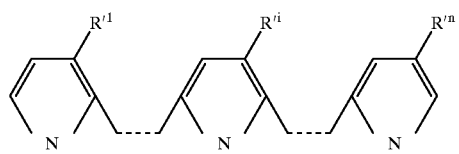

in which:

n is a non-zero integer and i is an integer ranging from 2 to n−1, and

R'1, R'i and R'n, which may be identical or different, each represent H or a functional group capable of covalently bonding with, or covalently bonded to, a first biological molecule or antiligand.

The functional groups bonded to a biological molecule or ligand are advantageously chose, before reaction with the latter, from the following set of functional groups:

$Y_p$—C—X where X represents H, OH, a substituted or unsubstituted lower O-alkyl radical, or a halogen, in particular Cl; $Y_p$—NHZ, Z representing H or an alkyl radical; $Y_p$—NH—CO—CF$_3$; $Y_p$—X where X corresponds to the above definition, p being an integer preferably equal to 0, 1 or 2; —Si(alkyl)$_3$, —Si(alkoxyl)$_3$ or an activated ester group such as COON-hydroxysuccinimide.

In particular, the functional groups bonded to a biological molecule are identical and consist, before reaction with the first biological molecule(s), or —(CH$_2$)—COOH, said first biological molecules or antiligands being chosen from peptides or peptide derivatives, in particular Gly-Phe, Phe-Pro and Phe-HEA-Pro, and from polynucleotides such as the oligonucleotide of sequence: CCTAAGAGGGAGTG.

The invention further concerns an electrically conductive, electroactive conjugated polymer of formula (II')

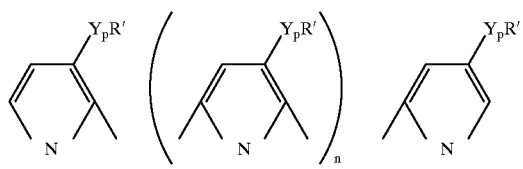

wherein n is an integer or zero, each R', which may be identical or different from one monomer unit to one another, is selected from the group consisting of H and functional groups capable of covalently bonding with, or covalently bonded to, a first biological molecule or antiligand with the proviso that at least one said R' of formula (II') represents one said functional group covalently bounded to one said first biological molecule or antiligand, each $Y_p$, which may be identical or different from one monomer unit to one another, is a coupling arm wherein p is zero or an integer, wherein said first biological molecule comprises a polynucleotide or peptide sequence.

Preferred polymers of formula (II') are the following:

polymers wherein p is 1, Y is selected from the group consisting of CH$_2$, CH$_2$—CH$_2$ and CH$_2$—CH$_2$—CH$_2$, and at least one said functional group, before being bonded to a first biological molecule or antiligand, is COOH;

polymers wherein p is 1, Y is selected from the group consisting of CH$_2$, CH$_2$—CH$_2$ and CH$_2$—CH$_2$—CH$_2$, and at least one said functional group, before being bonded to a first biological molecule or antiligand, is an activated ester; a preferred activated ester is selected from the group consisting of COON-hydroxysuccinimide, COON-hydroxyphtalimide, and COOpentafluorophenol;

polymers wherein p is 1, Y is (CH$_2$)$_m$CONH(CH$_2$)$_{m''}$ where each of m and m" identical or different is an integer ranging from 1 to 3, and at least one said functional group, before being bonded to a first biological molecule or antiligand, is an electrochemical probe; a preferred electrochemical probe is selected from the group consisting of ferrocene and quinone;

polymers wherein p is 1, Y is (CH$_2$)$_m$CONH(CH$_2$)$_{m''}$ where each of m and m" identical or different is an integer ranging from 1 to 3, and at least one said functional group, before being bonded to a first biological molecule or antiligand, is an electrochemical probe bound to an activated ester; preferred electrochemical probes and preferred activated esters are as set forth above;

polymers wherein p is 1, Y is (CH$_2$)$_m$CONH(CH$_2$)$_{m''}$ where each of m and m" identical or different is an integer ranging from 1 to 3, and at least one said functional group, before being bonded to a first biological molecule or antiligand, is NH$_2$ or any substituent possessing a terminal amino function NH$_2$;

polymers wherein p is 1, Y is (CH$_2$)$_m$CON(CH$_2$)$_{m'''}$ where m is an integer ranging from 1 to 3 and m''' is 2 or 3, and at least one said functional group, before being bonded to a first biological molecule or antiligand, is COOH.

The first biological molecule or antiligand is preferably selected from the group consisting of amino acids, peptides, oligonucleotides, antigens.

Another subject of the invention is the use of a conjugated polymer as defined above for detecting or assaying, in vitro or in vivo, a second biological molecule or ligand, which is different from the antiligand and which interacts specifically with the latter, said ligand being detected and/or assayed by observation and/or measurement of a potential difference or of a variation in current between the conjugated polymer not bonded to the ligand and the conjugated polymer bonded to the ligand.

In particular, the polymers of the invention are used to detect and/or assay an enzyme, such as a proteolytic enzyme and in particular carboxypeptidase A, or a polynucleotide, or to extract, in vitro or in vivo, a second biological molecule or ligand, which is different from the antiligand and which interacts specifically with the latter.

In one embodiment of the invention, the conjugated polymer is deposited on a conductive substrate, such as a metal or a carbon derivative, or in the form of a self-supporting film.

Lastly, the invention relates to an electrode and to a self-supporting film which consists of a conductive substrate such as a metal or a carbon derivative and of a polymer as defined above.

In one embodiment, the antiligand is specific for the ligand or target molecule. The antiligand is chosen in particular in order to form an antiligand/target molecule complex. By way of example, the complex may be represented in particular by any peptide/antibody, antibody/heptene, hormone/receptor, polynucleotidehybrids/polynucleotide, polynucleotide/nucleic acid couple or the like.

The term "polynucleotide" as used in the present invention denotes a sequence of at least five deoxyribonucleotides or ribonucleotides optionally comprising at least one modified nucleotide, for example a nucleotide containing a modified base such as inosine, 5-methyldeoxycitidine, 5-dimethylamino-deoxyuridine, deoxyuridine, 2,6-diaminopurine, 5-bromodeoxyuridine or any other modified base which allows hybridation. This polynucleotide may also be modified at the internucleotide bond (for example such as phosphorothioate, H-phosphonate and alkylphosphonate bonds), or on the skeleton, for example alpha-oligonucleotides (FR 2,607,507) or PNAs (M. Egholm et al., J. Am. Chem. Soc., (1992), 114, 1895–1897). Each of these modifications may be taken in combination.

The term "peptide" as used in the present invention refers in particular to any peptide of at least two amino acids, in particular a protein, protein fragment or oligopeptide, which is extracted, separated or substantially isolated or synthesized, in particular those obtained by chemical synthesis or by expression in a recombinant organism; any peptide in whose sequence one or more amino acids from the L-series are replaced by an amino acid from the D-series, and vice versa; any peptide in which at least one of the CO—NH bonds, and advantageously all of the CO—NH bonds, of the peptide chain is (are) replaced by one (or more) NH—CO bonds; any peptide in which at least one of the CO—NH bonds, and advantageously all of the CO—NH bonds, is or are replaced by one or more NH—CO bond(s), the chirality of each aminoacyl residue, whether or not this is involved in one or more abovementioned CO—NH bonds, being either conserved or inverted with respect to the aminoacyl residues constituting a reference peptide, these compounds also being referred to as immunoretroids, a mimotope.

Many classes of peptides may be grafted, as shown by the non-exhaustive list below: adrenocorticotropic hormones or fragments thereof; angiotensin analogs or inhibitors thereof (components of the renin-angiotensin system which regulate renal hypertension); natriuretic peptides; bradykinin and peptide derivatives thereof; chemotactic peptides; dynorphin and derivatives thereof; endorphins or the like; encephalins or derivatives thereof; inhibitors of enzymes (such as proteases); fragments of fibronectin and derivatives; gastrointestinal peptides; peptides associated with the release of growth hormones; neurotensins and the like; opioid peptides; oxytocin, vasopressin, vasotocin and derivatives; kinase proteins.

Peptides and polynucleotides have high biological activity, and are known to control many biological functions (A. S. Dutta, Advances in Drug Research, B. Testa Editor, Academic Press, New York, 1991, 21, 145). For example, peptides show very considerable therapeutic potential as agonist or antagonist receptors, and as very powerful inhibitors which bond strongly to enzymes, this being the principle upon which affinity chromatography is based. Moreover, by a selective hybridization reaction with other target nucleic acid fragments or nucleotides, polynucleotides may give rise to advantageous recognition phenomena, allowing in particular the development of novel gene scavengers. Thus, in order to detect and/or assay a target nucleic acid or nucleic acid fragment, a functionalized polymer which is at least partially bonded to an antiligand polynucleotide is placed in contact with a sample liable to contain the target, and the hybridization reaction is then detected if it takes place, either directly by measuring a potential difference or a variation in current between the non-bonded polymer and the bonded polymer which has reacted with the target, or indirectly by the same measurement as above, but using an additional detection polynucleotide which is capable of reacting with the target, said additional polynucleotide preferably adjoining the antiligand polynucleotide and being labeled with an electroactive molecule.

The term "antibody" as used in the present application refers to any monoclonal or polyclonal antibody, any fragment of a said antibody such as an Fab, Fab'2 or Fc fragment, as well as any antibody obtained by genetic modification or recombination.

Functionalization of the polypyrrole in the 3- or 4-position of the pyrrole ring may be carried out either on the monomer units with a subsequent polymerization step, or on the monomer units of a presynthesized polymer. Any suitable functionalizing agent may be used, provided that it comprises at least one reactive function capable of reacting with atoms 3 and/or 4 of the pyrrole ring. The functionalizing agent may thus be a monofunctional agent, provided that after the step of grafting on to the pyrrole ring the novel reactive function is introduced for subsequent reaction with the antiligand, and that this reactive function is multifunctional, such as bifunctional agents and in particular homo- or heterobifunctional agents. By way of example, the functionalizing agent is chosen from substituted or unsubstituted alkyl or alkoxyl or polyether chains ending with a group bearing a reactive function. The reactive function is represented in particular by a functional group such as a carboxylic, hydrazide, amine, nitrile, aldehyde, thiol, disulfide, iodoacetyl, ester, anhydride, tosyl, mesyl, trityl or silyl group or the like.

The formation of a conjugate resulting from the covalent coupling of an antiligand, for example a polynucleotide, with a functionalized polypyrrole according to the invention may be carried out according to the known, so-called direct or indirect methods.

For example, in the case of a polynucleotide, according to the direct method, a polynucleotide is synthesized having a reactive function on any site of the nucleotide chain such as, for example, the 5' end or the 3' end, or on a base or on an internucleotide phosphate, or on the 2' position of a sugar. The polynucleotide is then coupled with the polymer, which is prepared beforehand and contains a reactive function complementary to the above, that is to say one which allows the formation of a covalent bond by reaction between the two complementary reactive functions, one borne by the polynucleotide and the other by the functionalized polymer. For example, in a known manner, primary amines may be coupled with an activated carboxylic acid or an aldehyde or alternatively a thiol function may be coupled with a haloalkyl. Preferably, the reactive function of the polynucleotide for the coupling to the polymer is at the 5' or 3' end.

In the indirect coupling method, the polynucleotide and the polymer each bear a reactive function, it being possible for these reactive functions to be identical to or different from each other, these two functions not being complementary but being capable of reacting with an intermediate coupling agent which is a bifunctional reagent (homobifunctional if the two functions are identical or heterobifunctional if the two functions are different). Among the homobifunctional coupling agents which may be mentioned are DITC (1,4-phenylene diisothiocyanate), DSS (disuccinimidyl suberate) or analogs thereof. Among the heterobifunctional coupling agents which may be mentioned are SMCC (succinimidyl-4-(N-maleimidomethyl) cyclohexane-1-carboxylate) or SMPB (succinimidyl-4-(p-maleimidophenyl)butyrate), which are capable of reacting with a primary amine, on the one hand, and with a thiol, on the other hand.

BRIEF DESCRIPTION OF THE DRAWINGS

The invention will be better understood on reading the detailed description which follows, made with reference to the attached figures in which.

Figure 1A:
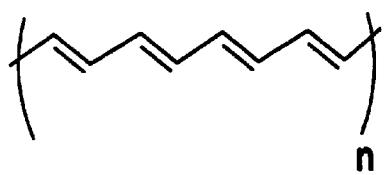
FIG. 1 represents examples of conjugated polymers such as 1) polyacetylene; 2) polypyrrole; 3) polythiophene; 4) polyphenylene; 5) polyaniline.
Figure 1B:
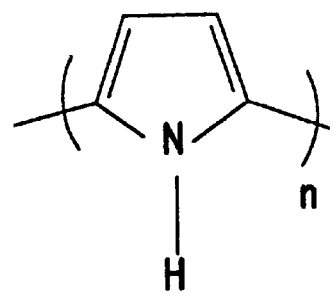
Figure 1C:
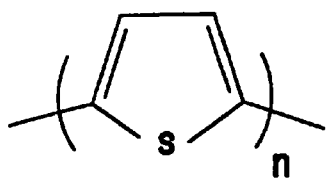
Figure 1D:
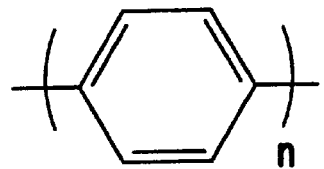
Figure 1E:
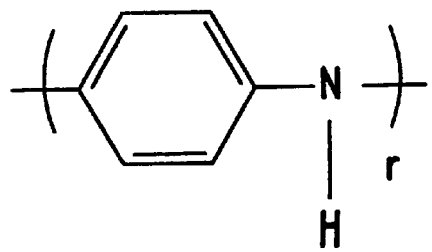
Figure 2A:
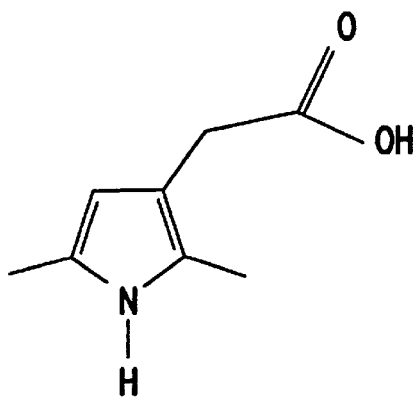
FIG. 2A represents a polypyrrole substituted in the 3-position with acetic acid (1) and FIGS. 2B, 2C, 2D, 2E and 2F represent polypyrroles substituted in the 3-position with various peptides (2 to 6 respectively)
Figure 2B:
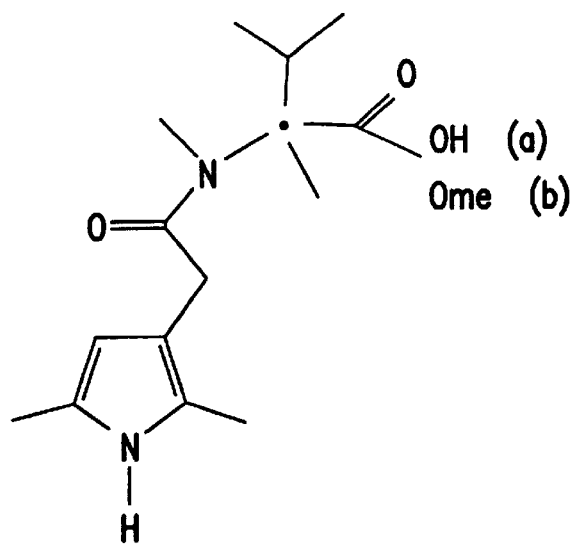
Figure 2C:
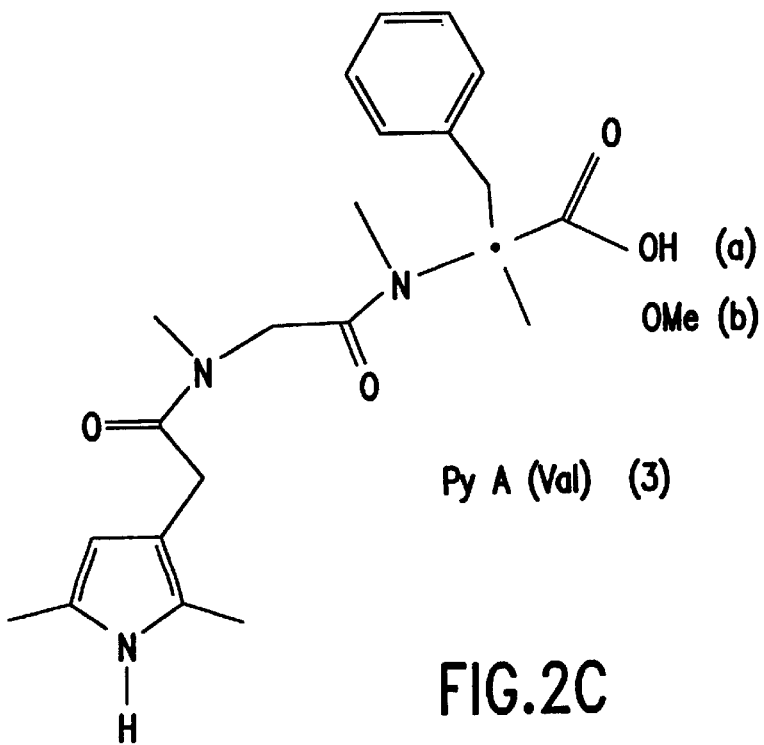
Figure 2D:
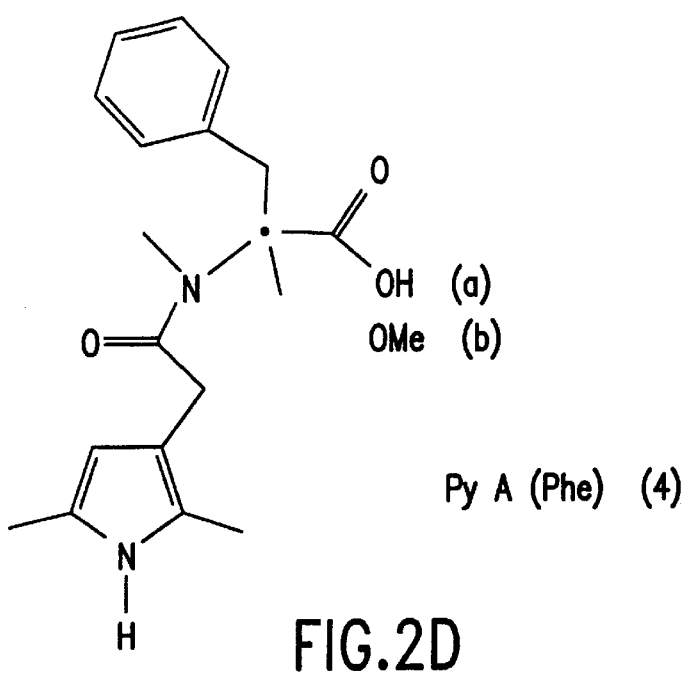
Figure 2E:
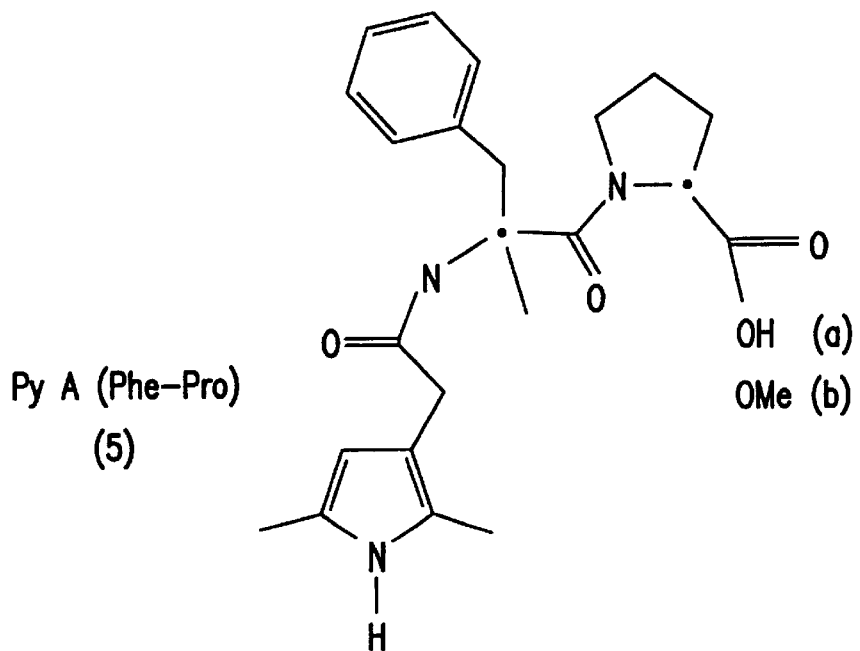
Figure 2F:
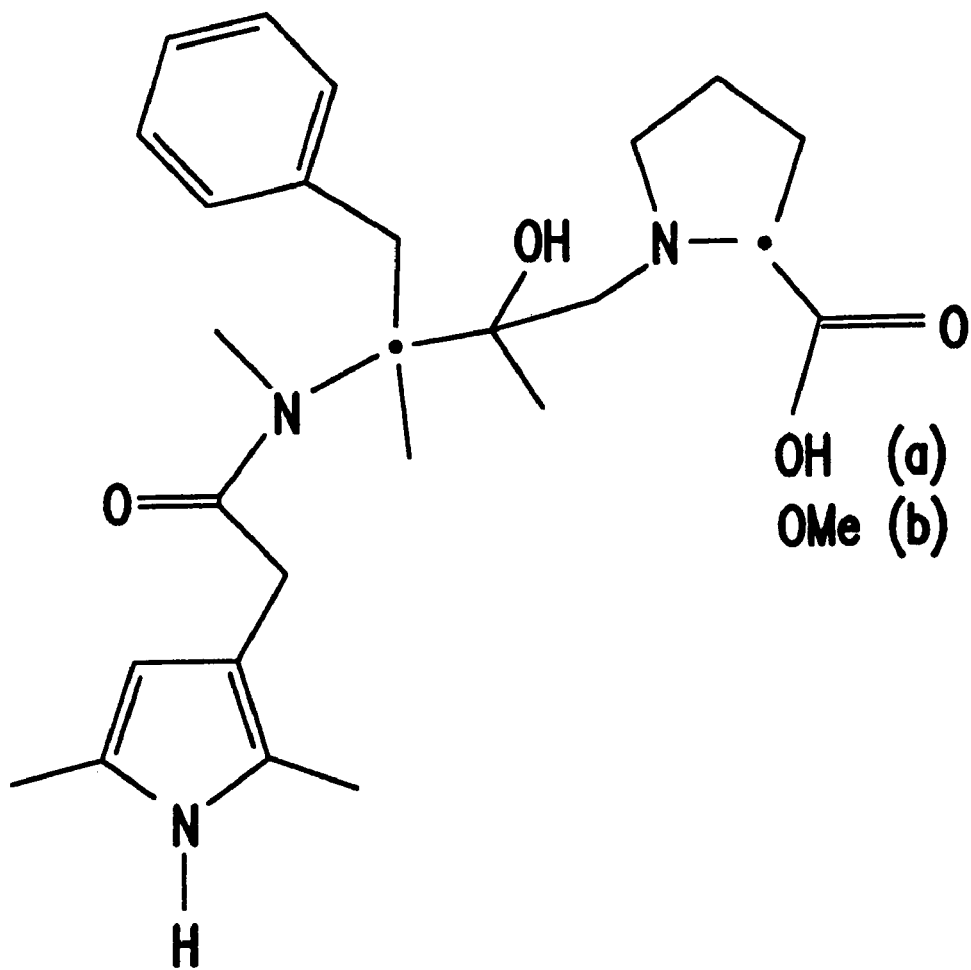

The polymers according to the invention may be used in particular for the detection of biologically active species which may be present in a sample and which may react with the antiligand or grafted antiligands. Indeed, as shown above, it is observed that the conjugated polymers functionalized in the 3-position of their heterocycle and on to which are grafted one or more antiligands, after reaction with one or more ligands, exhibit a modification of the electrochemical response with respect to a reference polymer which has not reacted with the ligand or ligands of a biological medium, this being visualized by a change in the oxidation potential. This variation in the oxidoreduction of the polymer in the electrochemical voltammogram inparts a scavenger-type function and may thus be used for a quantitative measurement of the biologically active species, either by variation of the potential, at fixed current, or by variation of the current at fixed potential, or alternatively by the production of field effect microelectrochemical transistors.

Moreover, the polymers of the invention may also be used for the extraction of biologically active species in solution. In many cases, the biologically active species in solution combines strongly with the antiligand grafted on to the polymer chain, such as a bioactive peptide or a polynucleotide, thereby making it possible to extract the biologically active species selectively from a medium. This type of extraction may be performed in vitro or even in vivo when the support polymer is biocompatible, such as polypyrrole for example.

Lastly, the polymers of the invention may be a source of release, from one medium into another medium, of biologically active species (enzymes or the like).

The functionalization of the electroactive conductive polymers of the invention, such as polypyrroles, by groups showing recognition with respect to compounds of biological interest may be extended to recognition of nucleic acids (NAs). Thus, the grafting of polynucleotides or oligonucleotides, ODN, along the conjugated chain of polymers should allow the discrimination of correspondings NAs or NA fragments within a biological medium. This recognition will be performed by selective hybridization between the ODN, grafted on to the polymer, and the corresponding NA present in the external medium, in which the film of functionalized polymer is immersed, just like the "peptide/enzyme" recognition described later. The "ODN/NA" complexation results in a modification of the physicochemical properties of the conjugated polymer, characterization of which will make it possible to confirm the presence of the desired NA.

The essential point relates to the nature of the physicochemical properties of the polymer destined for modification during the "ODN/NA" recognition. Indeed, in order to develop a rapid, sensitive and quantitative method for measuring the presence of NA, the aim of the present invention relates to the development of electroactive materials whose electrochemical response will be modified after "ODN/NA" hybridization. The modification will relate to a potentiometric-type variation, such as variation of the oxidation potential of the polymer, or an amperometric-type variation, by variation of the oxidation (or reduction) current observed at a given potential. These variations in electrochemical response may be measured quantitatively, the functionalized polymer films being used either as electrochemical scavengers of amperometric or potentiometric type, or alternatively in a field effect microelectrochemical transistor structure, as has been described above in the case of enzymatic recognition starting with peptides grafted on to polypyrrole. The advantages of measurements of this type are the speed, the sensitivity and the possibility of readily producing matrix cards of 2n measuring elements, containing n target and nontarget ODNs, which are thus capable of rapidly discriminating between the presence and absence of genes in a medium.

Just as in the case of the enzymatic recognition described above, a second essential point relates to the fact that in order to obtain an electrochemical response to a recognition phenomenon, the functionalization in the 3-position of heterocyclic (pyrrole) ring is essential.

In order to ensure a precise response of electrochemical type for these polymers, it is necessary for the functionalization of the conjugated chains to be compatible with considerable electroactivity of the functionalized polymer. The need for such an electroactivity requires, in the case of hydrophilic polyheterocycles such as polypyrrole, the functionalization to be performed in the 3-position of the pyrrole ring. The polymers of the invention are electroactive polymers in which either all of the monomer units are functionalized with an antiligand such as an oligonucleotide, or only some of the monomer units are thus functionalized. It is clearly understood that the monomer units may be functionalized with identical or different antiligands, and in the latter case the polymers of the invention may be used for the detection of several target ligands within the same sample. The polymers of the invention may be prepared by the following different routes:

a) Totally functionalized polymers.

In this route, the first step relates to the functionalization of the monomer, such as pyrrole, by an antiligand such as a given oligonucleotide. The second step then relates to the polymerization of this monomer, resulting in a film of polymer in which all the monomer units are functionalized.

b) Partially functionalized copolymers.

In the particular case of target nucleic acids, and bearing in mind their generally large size, the functionalization of all the monomer units, of small sizes, in the polymer is not necessary, and one of the routes thus relates to the production of a copolymer which involves, on the one hand, the functionalized monomer units described in a), and also pyrrole units which are not functionalized with the antiligand oligonucleotide.

c) Functionalization of a precursor polymer

The partial functionalization of a polymer film may also be performed starting with a conjugated polymer film, into which chemical groups compatible with the grafting of an antiligand such as an oligonucleotide are introduced beforehand. In this route, a monomer containing a grafting synthon is first produced, such as [N-3-hydroxysuccinimidepyrrole]. The synthon [N-hydroxysuccinimide] is known to allow the subsequent grafting of an oligonucleotide. This monomer is subsequently polymerized or copolymerized with another pyrrole derivative. The polymer film obtained is then immersed into the reaction medium containing an oligonucleotide, and the reaction to graft this oligonucleotide to the pyrrole monomers is then carried out. This grafting in fact only involves some of the pyrrole monomer units constituting the polymer.

Example 1

Synthesis of the Monomers

In the example described below, the polypyrrole (1) was chosen as conjugated polymer support on account of its biocompatibility (H. Naarmann, personnel communication). An acetyl spacer arm A is grafted between carbon atom 3 of the pyrrole ring and the peptide substituent in order to preserve the conductivity and the electroactivity of the corresponding functionalized polypyrrole. Various peptides, with their carboxylic end function unprotected or protected in methyl ester form, were chosen for their biological pertinence and were grafted on to a pyrrole-acetic acid monomer, PyA (1). Several mono- and dipeptides were grafted, and led to the following pyrrole derivatives, represented in FIG. 2: pyrrole-acetic acid, PyA (1), pyrrole (Glycine-dPhenylalanine), Py(Gly-DPhe) (2), for its capacity for complexation with proteolytic enzymes such as carboxypeptidase A (Sigma) and trypsin (Sigma) (J. R. Uren, Biochim. Acta, 1971, 236, 67), pyrrole(valine), Py(Val) (3), pyrrole(phenylalanine), Py(Phe) (4), pyrrole (phenylalanine-proline), Py(Phe-Pro) (5). Bulkier dipeptide derivatives may also be grafted, such as phenylalanine-hydroxyethylamine-proline, Py(Phe[HEA]Pro) (6), which is known to be an advantageous potential inhibitor for the protease associated with the HIV-1 virus of AIDS. These monomers were synthesized according to a described chemical route (D. Delabouglise, F. Garnier, Synth. Met., 1990, 39, 117). These monomers were purified and characterized by NMR, microanalysis and mass spectrometry.

Example 2

Polymerization

Figure 3:
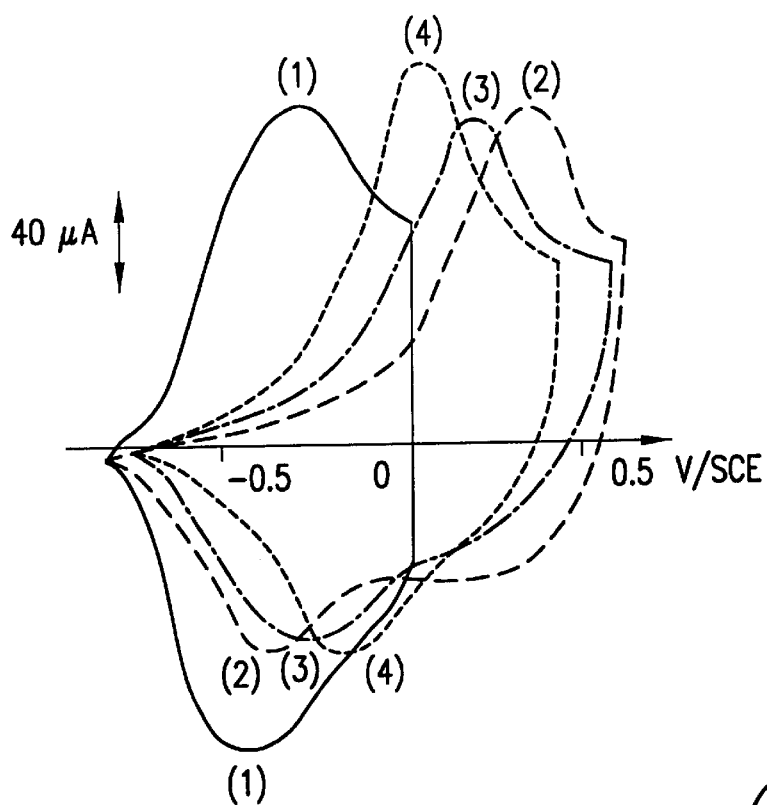
FIG. 3 represents the voltammograms of four functionalized polymers, identified below, in 0.5 M H2O—NaCl medium poly(pyrrole-acetic acid) in (1), poly(pyrrole(Gly-DPhe)) in (2), poly(pyrrole(Val)) in (3) and poly(pyrrole(Phe)) in (4)

These monomers were polymerized electrochemically on a 0.7 $cm^2$ platinum electrode, as well as on a platinum grille of surface area 10 $cm^2$ in propylene carbonate medium with 0.5 M NaCl, at a constant potential of 0.8 V/SCE. Thick polymer films are obtained, in thicknesses of up to 10 $\mu$m. As shown in FIG. 3, the electroactivity of these polymers was confirmed by cyclic voltammetry in 0.5 M H2O—NaCl medium, at a neutral pH of 7. The oxidation potential values, of the order of 0.30 V/SCE, close to that of unsubstituted polypyrrole, confirm the electroactivity of these polypyrroles functionalized with dipeptides.

Example 3

Recognition of Carboxypeptidase A

The specific properties of complexation of these polypyrroles with respect to proteolytic enzymes were analysed with carboxypeptidase A, with which (Gly-DPhe) is known to form stable complexes at neutral pH. Solutions of increasing concentration of carboxypeptidase A, ranging from 1 mg to 5 mg in 5 cm3 of 0.5 M H2O—NaCl, were analysed. When nonspecific electrodes such as unsubstituted polypyrrole, or poly(3, 4, 5 or 6) are immersed in this solution, a voltammogram identical to that obtained in Example 2 is observed, without any modification. However, when poly(pyrrole (Gly-DPhe)), poly (2), is used, the voltammogram shows a shift towards higher potentials, of 0.340 V/SCE for an initial zero amount of carboxypeptidase A up to a limit value of 0.500 mV/SCE for an amount of 5 mg of carboxypeptidase A in the solution. This result is given in FIG. 4, which shows the potential shift, attributed to steric hindrance and rigidification of the polypyrrole chain, produced during the complexation of the enzyme with the dipeptide borne by the polymer chain. The formation of this complex between enzyme and poly(pyrrole-dipeptide) was confirmed by the release of the enzyme into acidic medium, at pH=3, as is performed conventionally in affinity chromatography (I. M. Chaiken, M. Wilchek, I. Parikh, Affinity Chromatography and Biological Recognition, Academic Press, New York, 1983). The released enzyme was characterized conventionally by the Bradford test, involving measurement of the enzymatic activity with Coomassie brilliant blue, and by the use of a standard bovine serum albumin. When a poly(Gly-DPhe) film is used containing 5×10-6 monomer units, corresponding to a polymerization charge of 1 coulomb, a significant amount, 400 micrograms, of carboxypeptidase A was obtained after release into an acidic medium. Considering the size of this enzyme, 307 amino acid units, this amount of released enzyme shows that about 1 molecule of enzyme is complexed per 200 monomer units of (pyrrole-dipeptide), which appears to be reasonable given the difference in size (of about a factor of 100). This result also shows that the enzyme must be distributed inside the polymer film, thereby demonstrating the permeability of this film with respect to the enzyme. Comparable results were obtained when trypsin was used as the enzyme.

Figure 4:
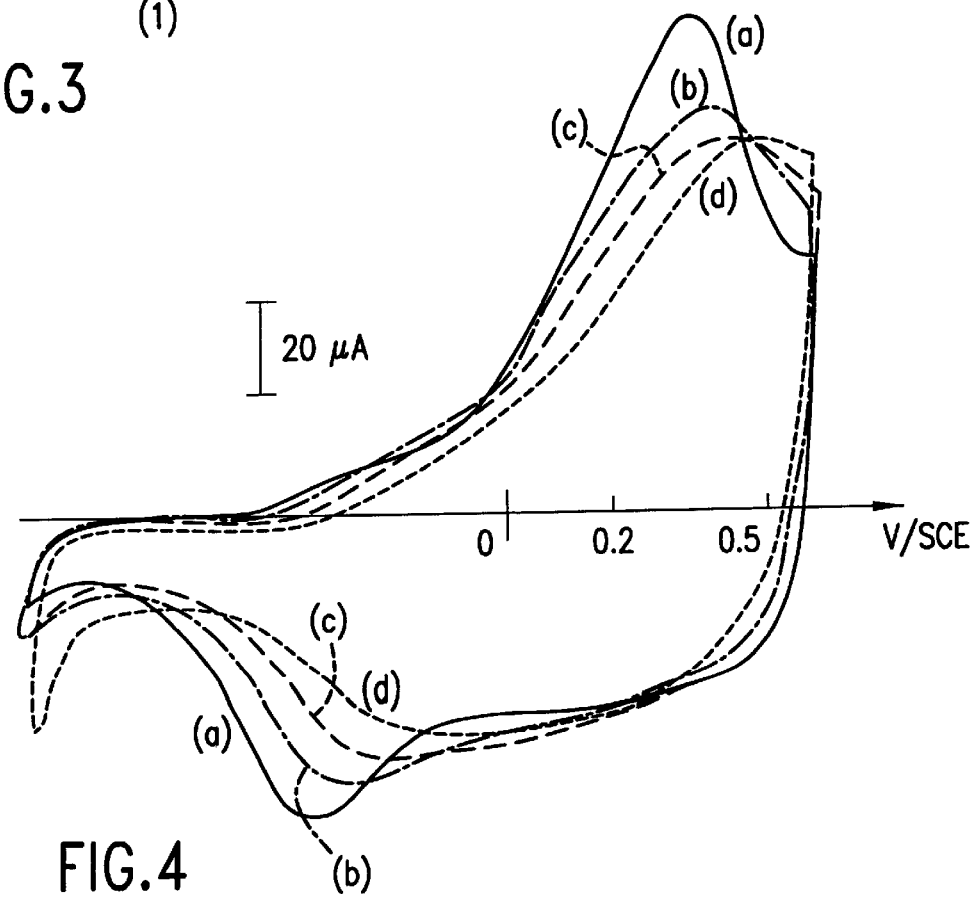
FIG. 4 represents the voltammogram of poly(2), in 0.5M H$_2$O—NaCl medium, in the presence of carboxypeptidase A at concentrations respectively of 0.0 mg in 5 cm$^3$ of electrolyte (a), 1.2 mg in 5 cm$^3$ of electrolyte (b), 2.4 mg in 5 cm$^3$ of electrolyte (c) and 5.0 mg in 5 cm$^3$ of electrolyte (d)
Figure 5:
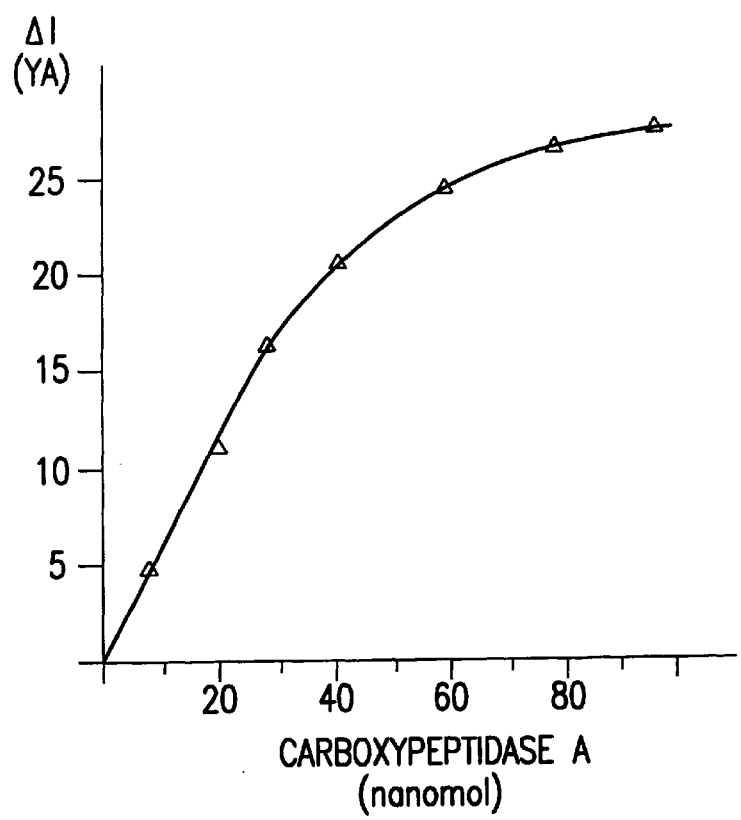
FIG. 5 corresponds to the amperometric response of an electrode, poly(2), as a function of the amount of enzyme, carboxypeptidase A, in nanomoles, present in the medium. The linear relationship between the current observed and the amount of enzyme, at a potential of 0.3 V, is given with reference to a saturated calomel electrode.
Figure 6:
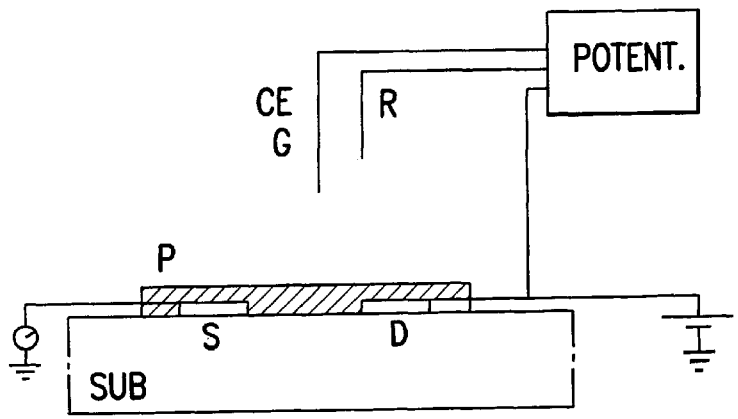
FIG. 6 is a theoretical diagram of a field effect microelectrochemical transistor for the (amplified) detection of the presence of a biological species recognized by a functionalized conductive polymer. The abbreviations which follow have the respective meanings: P, polymer. Sub, substrate. S and D, source and drain electrodes respectively. CE, counterelectrode acting as a grille G. R, reference electrode. Potent., potentiostat.

At a given electrode potential, as seen in FIG. 4, a variation in current is observed as a function of the enzyme concentration. This result corresponds to the amperometric response of the electrode, and one of the advantageous characteristics of this response relates to its linearity with the concentration of enzyme, as seen in FIG. 5. Such a linear relationship makes it possible to propose a quantitative assay of the biological species in solution, either by the use of a scavenger of electrochemical type, or by the development of a field effect transistor, represented schematically in FIG. 6. The operating principle is as follows. The polymer is made on the source and drain electrodes, which are arranged on a substrate. This assembly is immersed into the solution to be analysed, and a counterelectrode in this same medium represents the grille of this transistor. When this grille electrode is placed at a potential at which the variation of the voltammogram as a function of the enzyme concentration is at a maximum, at about 0.2 V in the case represented in FIG. 4, the conductivity of the polymer varies considerably with the enzyme concentration. A potential then applied between source and drain electrodes makes it possible to obtain an amplified signal, this transistor operating according to the principle of a field effect transistor.

Example 4

Controlled Release of an Enzyme

An additional advantageous characteristic of these electrodes relates to the fact that it has been shown in the literature that poly(pyrrole-acetic acid), or poly(1), releases protons into the electrolytic medium when it is subjected to electrochemical oxidation (P. Baerle et al. Adv. Mater., 1990, 2, 490). Large variations in pH may be observed in a small electrolytic volume, up to values of the order of 3. This release of protons is also observed when the carboxylic function is distanced from the pyrrole ring, such as is the case for an unprotected amino acid or peptide grafted on to the pyrrole. Two routes exist for the controlled release of protons; either the use of a peptide whose carboxylic end function is not protected, COOH, or the use of a copolymer between pyrrole-acetic acid and pyrrole-protected peptide. An example of this second route is given. A copolymer between Py(A), (1), and Py(Gly-DPhe), (2), was prepared electrochemically, under the same conditions as above. When subjected to electrooxidation at 0.3 V/SCE, this poly(1, 2) copolymer leads to a large variation in pH of up to pH=4 in the region of the electrode.

Starting with this poly(1, 2) copolymer or starting with the poly(2) polymer whose carboxylic function is free, two processes may be carried out for the extraction; a batchwise process and a continuous process.

a) Batchwise process

This process consists in using a membrane or electrode based on the abovementioned materials, and in placing it in contact with the medium in which the desired biologically active species coexists with other species. The selective affinity provided by the grafted peptide with respect to this desired species will cause complexation of the latter with the peptide grafted on to the polymer of the electrode or of the membrane. This membrane or electrode is then removed from the analysis medium and introduced into another medium, referred to as the recovery medium. In this recovery medium, containing a support salt of NaCl type, the electrode or membrane is subjected to an electrochemical oxidation, which causes the expulsion of protons, by means of the carboxylic acid groups, up to a pH which is sufficient for the dissociation and release of the desired species.

b) Continuous process

The poly(1, 2) copolymer, or the poly(2) polymer with its carboxylic function free, is prepared in membrane or electrode form, optionally using a polycationic or polyanionic support polymer of the polystyrene sulfonate type of alternatively perfluoro membrane type such as NAFION. This possibly composite electrode or membrane constitutes the junction between two compartments A and B, as represented schematically in FIG. 7. An example of the continuous extraction of carboxypeptidase A by this process is described below.

Figure 7:
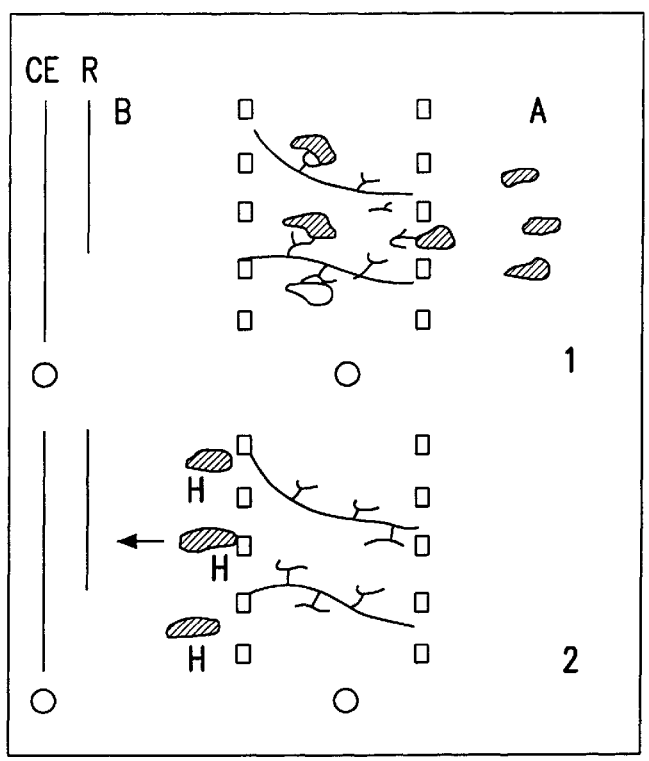
FIG. 7 is a theoretical diagram of a 2-compartment electrochemical cell containing a functionalized polypyrrole membrane, for the extraction of biological species recognized by a substituent grafted on to an electroactive conjugated polymer chain.

In the case outlined in FIG. 7, the bioselective element consists of a poly(1, 2) copolymer described above, polymerized in a NAFION (Aldrich) membrane, obtained by evaporation of 10 $\alpha$l of a 5% solution of NAFION in a mixture of linear higher alcohols (Aldrich) on a very fine platinum grille. The film of NAFION resulting therefrom, which has a thickness of about 5 $\alpha$m, then serves as a support for the electropolymerization of the poly(1, 2)copolymer, resulting in a poly(1, 2)-NAFION electroactive composite membrane.

In a first step 1, 10 grams of carboxypeptidase A are introduced into the compartment A, in 0.5 M H2O-NaCl medium. A complexation on the [poly(1,2)]-NAFION composite membrane then occurs immediately on the peptide units of (2), as described above in Example 3. An oxidation is subsequently performed, using a counter-electrode and a reference electrode which are introduced into the compartment B. In a second step 2, the electrochemical oxidation leads to the release of protons in this compartment B, up to a pH of about 4, and to the immediate release of carboxypeptidase A. 1.2 grams of carboxypeptidase A were then recovered in the compartment A over one cycle of this continuous process, as was determined by assaying the enzyme activity.

These results thus confirm the phenomenon of recognition of these electrodes with respect to enzymes, as well as their capacity to extract these enzymes. This behavior is linked in a one-to-one manner with the chemical nature of the dipeptide grafted on to the polypyrrole chain.

Example 5

Synthesis of a Polypyrrole Functionalized with a Polynucleotide or Oligonucleotide This synthesis is carried out according to the following 3 steps.

a) Synthesis of the [N-3-hydroxysuccinimidepyrrole] monomer 0.4 mol of pyrrole-acetic acid, (I), 30 ml of chloroform and 0.4 mol of N-hydroxysuccinimide, NHS; (II) are added to a 3-necked flask. The mixture is set stirring and a solution of 0.4 mol of dicyclohexylcarbodiimide, DCC, in 20 ml of chloroform is then added dropwise. After stirring for 2 hours, a white solid is formed, which is filtered off and washed with chloroform. After evaporation and washing with acetonitrile in order to get rid of unnecessary reaction products, the product is recrystallized from chloroform. The desired compound, [N-3-hydroxysuccinimidepyrrole] (III), is thus obtained in the form of a white powder.

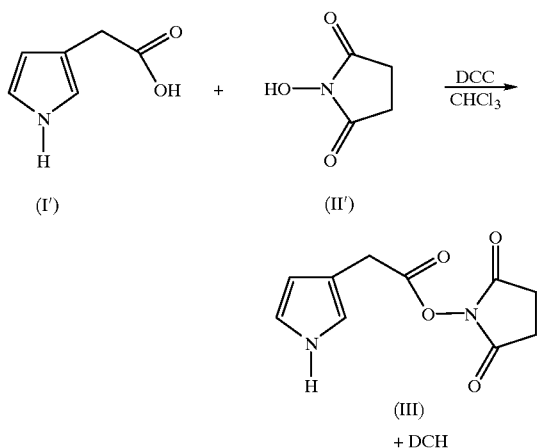

Melting point, m.p.=135° C. 1H NMR (ppm): (NH, 1H, 9, s); pyrrole (2H, 6.7, m): pyrrole (1H, 6.1, s); $CH^2$ (2H, 3.8, s); hydroxysuccinimide (4H, 2.8, s).

b) Synthesis of the polymer by electropolymerization

The electropolymerization solution contains 0.5 M LiClO4 and 0.1 M monomer (III) in acetonitrile. The electropolymerization is performed on a platinum electrode of surface area 0.7 $cm^2$, at a potential of 0.9 V relative to a saturated calomel electrode, SCE, using an electropolymerization charge of 30 mC. A black film appears on the electrode, corresponding to poly(III), the thickness of which is about 200 nm.

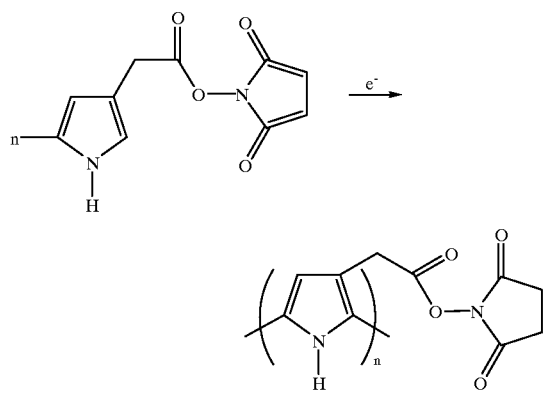

Figure 8:
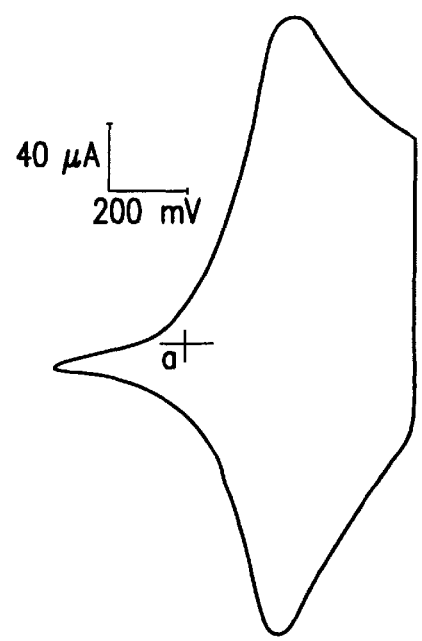
FIG. 8 represents the voltammogram of poly[N-3-hydroxysuccinimidepyrrole], in 0.1 M LiClO$_4^-$ acetonitrile medium with a saturated calomel reference electrode, showing high electroactivity and high electrochemical reversibility.

The electroactivity of this polymer was analyzed in a 0.5 M LiClO4-acetonitrile medium, showing an oxidation peak at 0.28 V/SCE and a reduction peak at 0.24 V/SCE, as seen in FIG. 8. The small separation between these oxidation and reduction peaks, 40 mV, confirms the very great electroactivity and reversibility of this polymer.

c) Grafting of an oligonucleotide ODN

The above electrode bearing the polymer film is immersed in a reaction medium formed of a mixture of dimethylformamide with 10% 0.1 M borate buffer at a pH of 9.3 and 26.2 nanomol of the 14-base oligonucleotide, ODN, containing the sequence CCTAAGAGGGAGTG as well as a 5' amine function on which the coupling reaction will be performed with the N-hydroxysuccinimide group borne by the pyrrole units of the polymer. This coupling reaction takes place over 2 hours. The grafting is also accompanied by hydrolysis of the succinimide groups, which are not substituted with the oligonucleotide, in acetic acid. The polymer obtained on the electrode thus corresponds to a poly ([pyrrole-ODN][pyrrole-COOH]) copolymer.

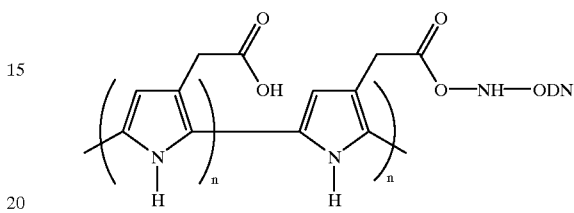

Example 6

Characterization of the Recognition Phenomenon

Figure 9:
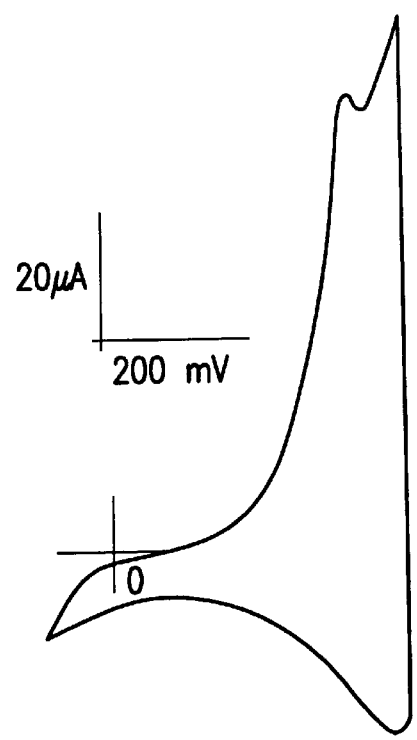
FIG. 9 represents the voltammogram of a poly(pyrrole-ODN][pyrrole-COOH]) copolymer electrode, with ODN of sequence CCTAAGAGGGAGTG as polynucleotide or oligonucleotide. No modification is observed after incubation of this polymer with a non-target sequence, GGTGATAGAAGTATC.
Figure 10:
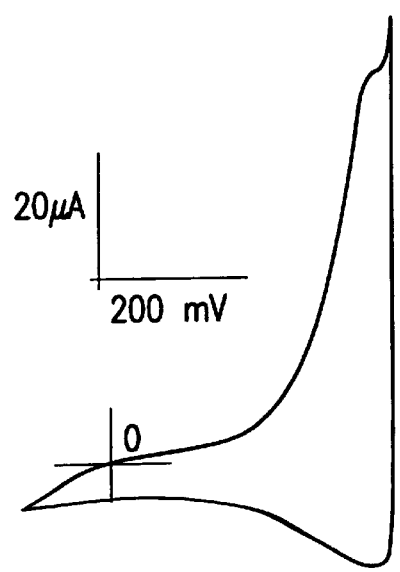
FIG. 10 represents the voltammogram of a poly([pyrrole-ODN][pyrrole-COOH]) copolymer electrode, with the sequence: CCTAAGAGGGAGTG as oligonucleotide ODN. This electrode was incubated in the presence of a target, 335 nmol CACTCCCTCTTAGG, at 37° C. for 2 h. This electrode was then rinsed and analysed in electrochemical medium. A potential shift is observed with respect to the previous voltammogram.
Figure 11:
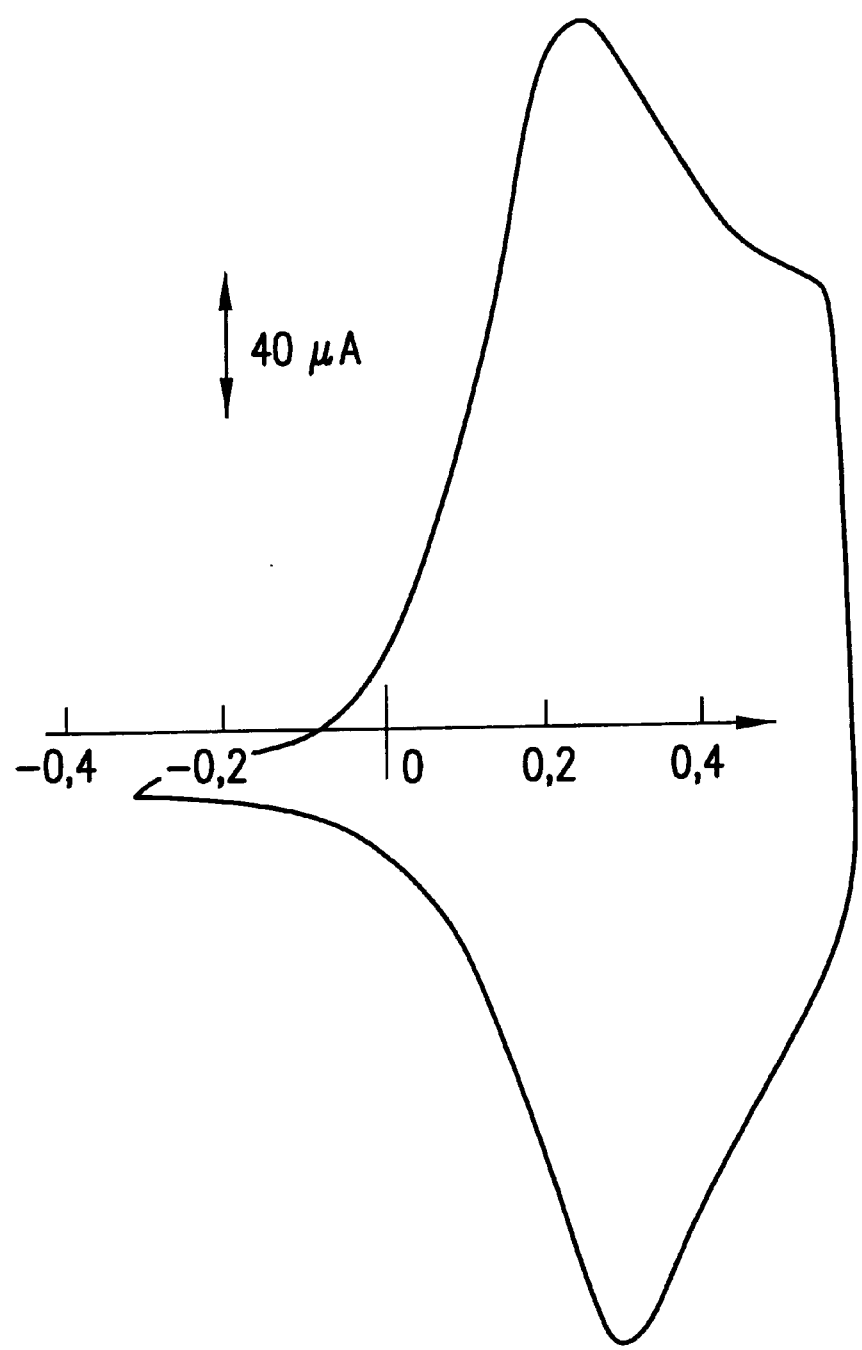
FIG. 11 represents the cyclic voltammogram of a film P[Py-NHR], poy(B), (0.9 V/SCE with grown charge 40 mCcm$^{-2}$, in 0.1 M LiClO$_4$ acetonitrile solution, scan rate 20 mVs$^{-1}$.
Figure 12:
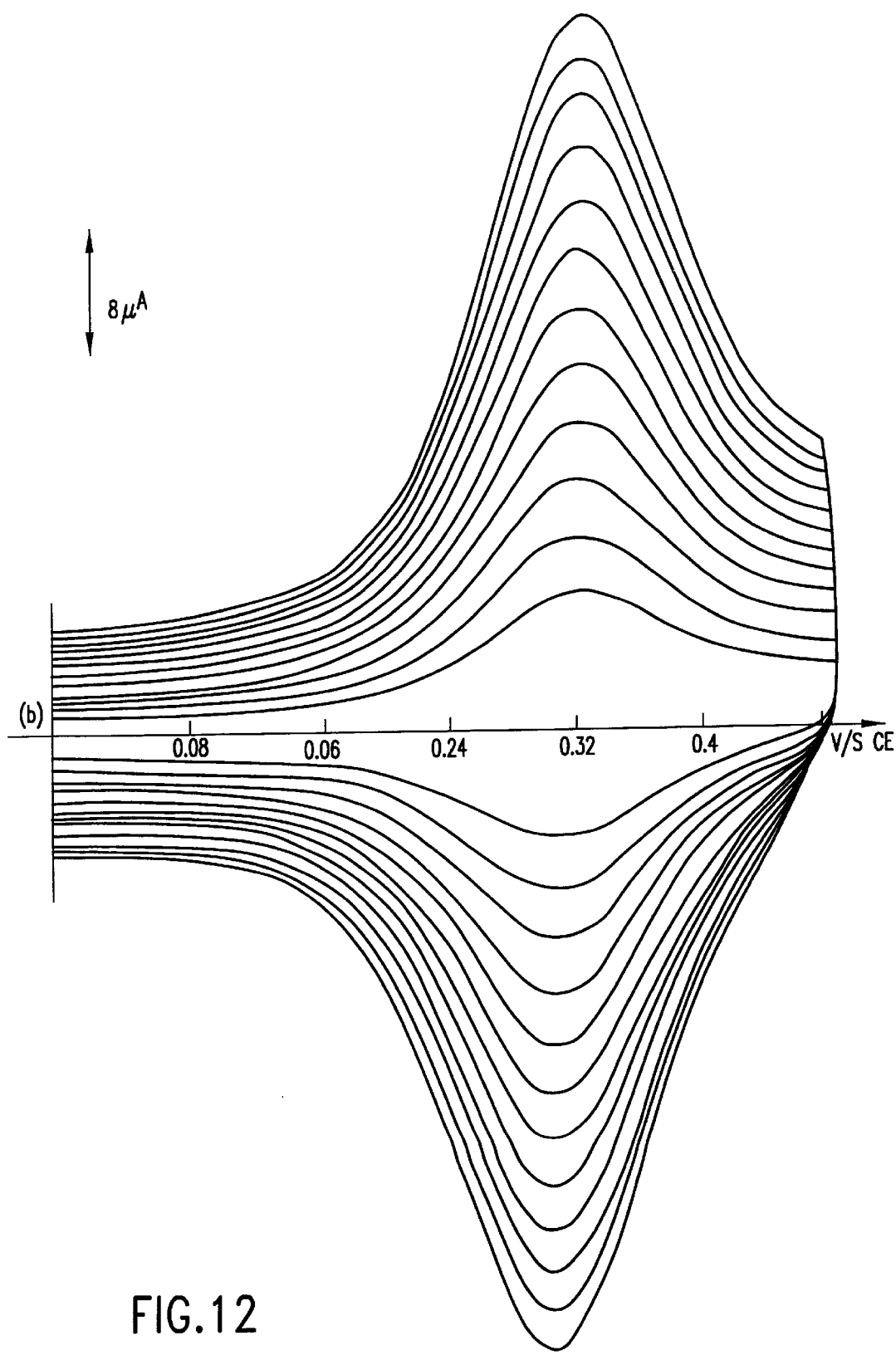
FIG. 12 represents the cyclic voltammograms of a thin film of P[Py-FeCp2], poly(C) (thickness, e=1 nm) in CH$_3$CN/0.1 M LiClO$_4$ at scan rates in the range of 5–130 mVs$^{-1}$.
Figure 13:
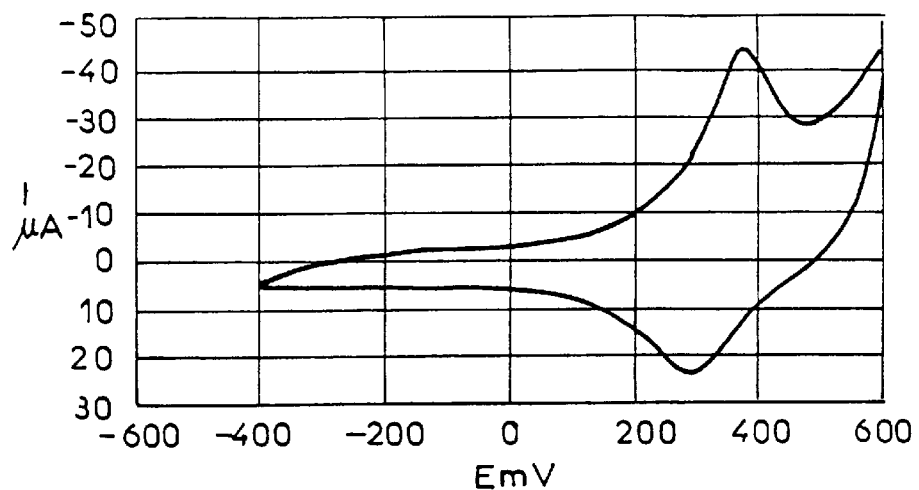
FIG. 13 represents the voltammogram of copoly[pyNHFe (Cp)$_2$-pyNHP], copoly[(B)(C)] in an aqueous solution of 0.5M NaCl.
Figure 14:
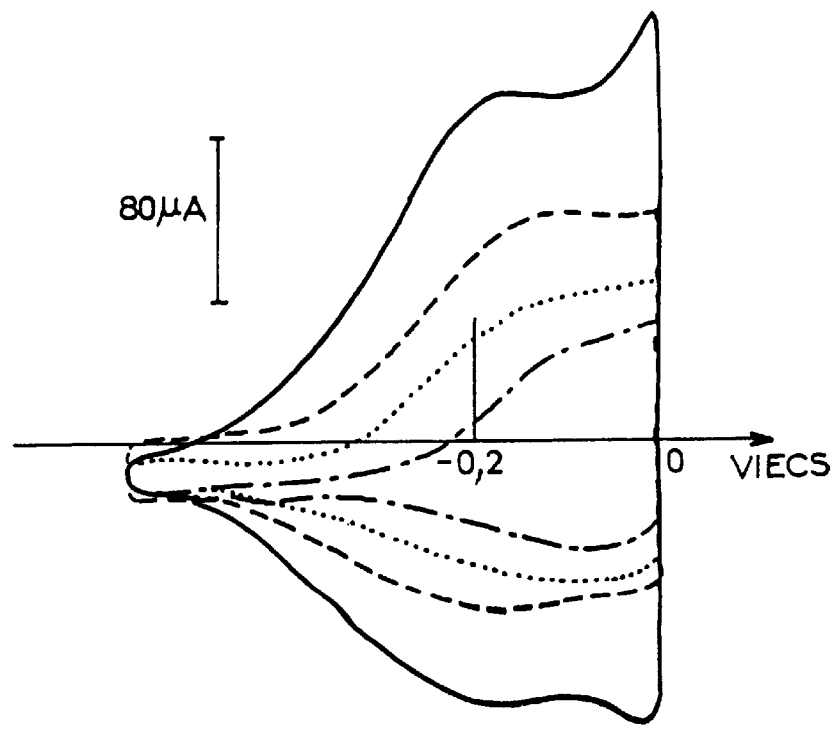
FIG. 14 represents an electrochemical caracterisation of films of PEG and of poly[pyrrole-ODN, pyrrole-COOH] in aqueous medium, before (1) or after hybridization with ODN for different target ODN proportions [(2) 66 nmoles, (3) 165 nmoles, (4) 500 nmoles)].
Figure 15:
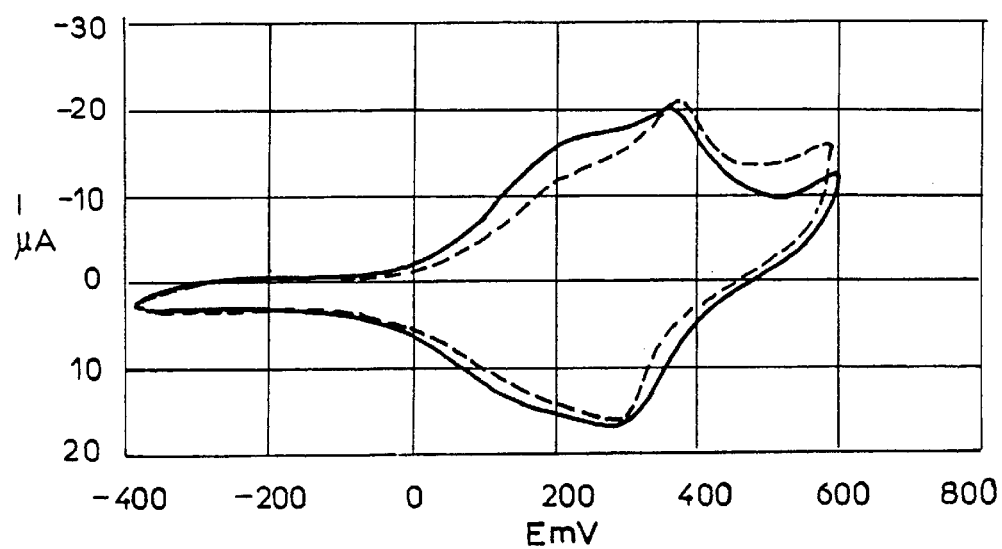
FIG. 15 represents voltammograms of copoly[pyNHFe (Cp)$_2$, PyODN], in aqueous solution of 0.5M NaCl. Initial voltammogram and after incubation with non-target ODN (–) and after incubation with complementary target ODN (0.02 nmole/5 ml) (--).

The recognition phenomenon was confirmed by electrochemical characterization of the poly([pyrrole-ODN] [pyrrole-COOH]) polymer film obtained in Example 5c. The electrochemical analysis was first carried out directly on the electrode obtained after synthesis, and then after this electrode had been placed in the presence of the target ODN and the non-target ODN. The hybridization reaction of this polymer was thus performed in the presence of complementary ODN (target) and non-complementary (ODN) (non-target), in an aqueous solution buffered with PEG. Incubation is carried out at 37° C. for 2 hours, either in the presence of target ODN CACTCCCTCTTAGG, at a concentration of 335 nanomol, or in the presence of non-target ODN GGTGATAGAAGTATC, at a concentration of 272 nanomol. After reaction, the films were rinsed with the PEG buffer and analyzed by cyclic voltammetry. The voltammograms obtained are represented in FIGS. 9 and 10. The results show firstly, in FIG. 9, that after synthesis and before being placed in the presence of the target or non-target sequence, the polymer shows a reversible oxidation peak at 0.34 V/SCE, confirming the electroactivity of this functionalized polymer. After the incubation reaction in the presence of the non-target sequence, and after rinsing, the voltammogram obtained shows no modification. On the other hand, when this polymer is incubated in the presence of the target, the voltammogram obtained, FIG. 10, is different, with an increase of the oxidation potential to 0.40 V/SCE, equivalent to an increase of 60 mV. This increase is entirely indicative of a hybridization which has taken place between the ODN and the corresponding target. This increase in the oxidation potential is attributed to a phenomenon of complexation of the arm hanging along the polypyrrole chains, thus accompanied by an increase in the energy required to oxidize this polymer.

This result confirms that this novel class of electroactive materials, of conjugated polyheterocycles substituted in the 3-position with an oligonucleotide, effectively gives rise to a phenomenon of recognition of complementary DNA, and, moreover, that these materials allow, electrochemical reading of this selective hybridization. This electrochemical reading opens the way to gene scavengers of electrochemical, amperometric or potentiometric type, and, moreover, to gene scavengers of field effect microelectrochemical transistor type, based on an amperometric response.

Example 7

Synthesis of Preferred Polymer (A)

1) Synthesis of 1-tosyl pyrrole

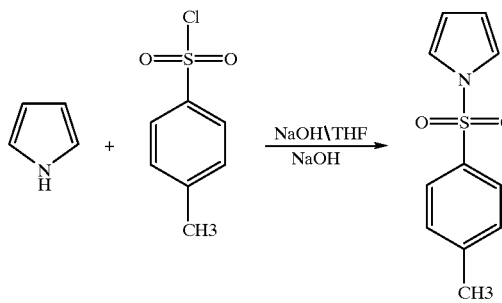

Method 8 ml of pyrrole that has been previously distilled in 100 ml of THF is put into a 500 ml twin necked flask fitted with a magnetic stirrer and a condenser. After a quarter of an hour, when the mixture is homogeneous, 6 ml of tetrabutyl ammonium hydroxide (the reaction catalyst) is added. The colourless solution becomes orange. While the mixture homegenises, a 50% solution of sodium hydroxide is prepared (62.5 g in 125 ml of water), which is then added drop by drop to the mixture. This operation causes a proton to leave the nitrogen on the pyrrole so that substitution by the tosyl group is optimised.

The mixture is stirred for 15 minutes and the tosyl chloride solution is added in excess (32 g in 100 ml of THF) and drop by drop so as to have an excess of radicals and to encourage the reaction. Vigorous stirring is maintained during the addition and then for 1 hour. The product changes from an orange colour to a brown colour.

When the stirring is stopped, 2 phases are seen to form. After adding 300 ml of water, they are allowed to separate. The aqueous phase is extracted with ethyl acetate. The first organic phase is evaporated to remove the THF, the second organic phase is added to it and the ethyl acetate is evaporated.

The crystals are dissolved in dichloromethane and this organic phase is washed with water until the washing water is neutral. The organic phase is dried over anhydrous $MgSO_4$, filtered and the dichloromethane evaporated.

Recrystallisation is carried out to purify the crystals. The 1-tosyl pyrrole is dissolved in 300 ml of heptane by heating under reflux for 30 minutes. On filtering at a Buchner, the impurities (coloured brown) remain on the filter and a pale yellow product is obtained which gives white crystals once the solution has cooled.

22.3 g of crystals are obtained which is a yield of 87.5%.

2) Synthesis of 3-acetyl 1-tosyl pyrrole

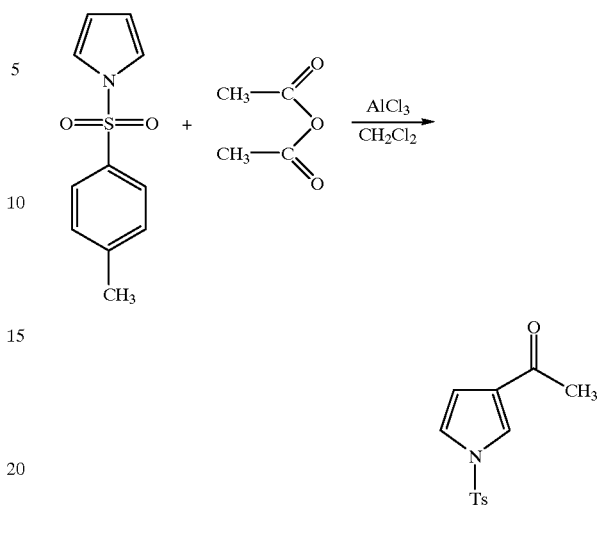

Method 94.6 g of aluminium chloride (the reaction catalyst) and 600 ml of dichloromethane are mixed in a three-necked flask fitted with a magnetic stirrer and a condenser with a $CaCl_2$ moisture guard. The mixture is stirred until homogenous and then 37.5 ml of acetic anhydride (reactant in excess) is added drop by drop.

After a quarter of an hour, a brown transparent solution is obtained. A solution of 1-tosyl pyrrole (31.4 g in 80 ml of dichloromethane) is added drop by drop.

The reaction is allowed to proceed for an hour under agitation and at ambient temperature. The entire mixture is then poured into 500 ml of iced water. After allowing it to separate, the organic phase is extracted and the aqueous phase is washed with dichloromethane. This operation is repeated several times. The organic phases are washed with 1M NaOH to make the $Al^{3+}$ soluble and remove it with the water washings. At the end of the washing process, the neutral pH of the aqueous phase is checked.

The organic phases are dried over anhydrous magnesium sulphate and the dichloromethane is evaporated.

A recrystallisation is then carried out to purify the crystals obtained: the 3-acetyl 1-tosyl pyrrole is dissolved in heptane (500 ml). It is heated under reflux, filtered at a Buchner and the filtrate placed in a freezer. The material in the bottom of the flask is crystallised several times. The heptane is evaporated and violet crystals are obtained.

19.61 g of crystals are obtained, a yield of 52.4%.

3) Synthesis of methyl 1-tosylpyrrole-3-acetate

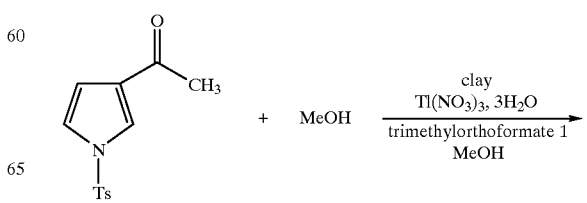

-continued

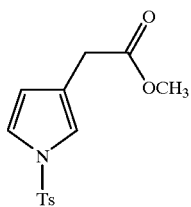

Method

In a first step, the esterification catalyst is prepared. This consists of depositing Tl(NO$_3$)$_3$.3H$_2$O on clay. In a single necked flask, 55 ml of trimethyl orthoformate, is mixed with 45 ml of methanol and 22 g of Tl(NO$_3$)$_3$.3H$_2$O. This is stirred for 5 minutes and then 45 g of clay is added in such a way that a greyish beige suspension is obtained. This is stirred for a further 15 minutes and the solvents evaporated using a rotary vaporiser. Once it is well dried, the catalyst on clay is recovered in the form of a beige powder.

One can then progress to the synthesis of the ester. 11 g of acetyl tosyl pyrrole (dissolved in 400 ml of methanol) is mixed with the thallium catalyst on clay in a single necked flask. Taking the precaution of fitting a condenser, it is left to stir overnight.

The stirring is topped and two phases can then be seen (an orange phase above and a thick phase with a greyish beige colour below) The organic phase is recovered after filtration. The methanol is evaporated using a rotary vaporiser and then CH$_2$Cl$_2$ and water are added. The aqueous phase is washed with CH$_2$Cl$_2$ and the organic phase (a blood red colour) with water in order to remove the thallium salts. This organic phase is dried over MgSO$_4$ and evaporated using a rotary vaporiser.

As the reaction can give rise to several by-products such as

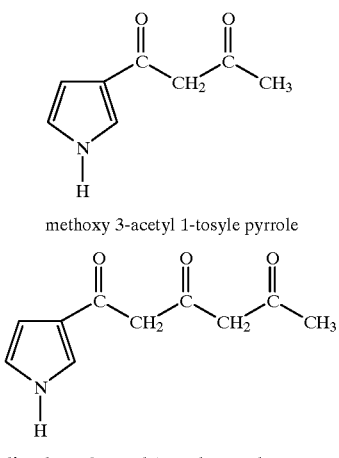

the desired ester will be isolated on a silica gel column. Having made a chromatographic plate it may be noted that this ester is already isolated but nevertheless a column is used to remove excess clay (which remains at the head of the column). For the column, it is necessary to use a mixture of two solvents of different polarity as eluent since using a suitable composition of the two solvents, better separation is obtained. Therefore a mixture made up of 30% ethyl acetate (polar solvent) and 70% heptane (non-polar solvent) is used. The solvent is evaporated and a yellow oil is collected.

9.23 g of ester is obtained being a yield of 75.6%.

4) Synthesis of pyrrole-3-acetic acid

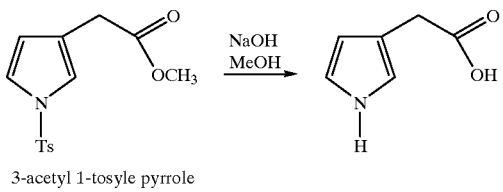

3-acetyl 1-tosyle pyrrole

Method 7.65 g of 1-tosyl pyrrole-3-acetate, 100 ml of methanol and 100 ml of 5M sodium hydroxide are mixed in a single necked flask fitted with a condenser. The medium is stirred and heated under reflux for 2 hours 30 minutes. It is left to cool to ambient temperature. The sodium carboxylate is obtained. The methanol is evaporated and 100 ml of ether and water are added. Two phases separate, with the aqueous phase containing the carboxylate. This phase is washed several times with ether. Then, very slowly, concentrated HCl is added, taking care to control the temperature of the reaction medium using an ice bath in order to prevent polymerisation. The product is then to be found, in the form of an acid, in the organic phase. The aqueous phase is extracted with ether and the organic phase is dried over sodium sulphate.

A rotary vaporiser is then used and a silica gel column is used to separate the acid and the clay. The solvent is evaporated and a yellow liquid is obtained that crystallises rapidly. It is advisable to store it in ether in the freezer in order to restrict the risk of polymerisation.

2.7 g of product is obtained representing a yield of 82.6%.

Example 7

Synthesis of Preferred Polymer (B)

1) Synthesis of 3-acetate N-hydroxyphthalimide

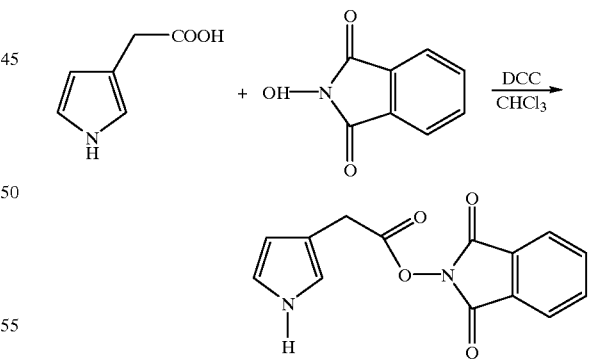

Method 1.38 g of pyrrole-3-acetate acid, 1.98 g of N-hydroxyphtalimide and 50 ml of chloroform are mixed in a three necked flask. Using an addition ampoule, a solution of DCC (2.67 g of DCC in 30 ml of CHCl$_3$) is slowly added.

During the addition of the DCC, the mixture forms a solution.

It is left to stir overnight. DCU forms. It is filtered and the CHCl$_3$ evaporated. A new white precipitate of DCU forms.

It is placed in the refrigerator for 1 hour, filtered and evaporated. This operation is repeated until the DCU is completely removed.

Plate chromatography is carried out using a dichloromethane/methanol 2/98 solvent. A mark corresponding to NHP is seen to appear. To remove it, a silica gel column is used with the same eluent as that used for the plate. The product is recrystallised in chloroform.

A product of mass 1.04 g is obtained representing a yield of 35%.

Example 8

Synthesis of Preferred Polymer (C)

1) Synthesis of β-ferrocene ethylamine

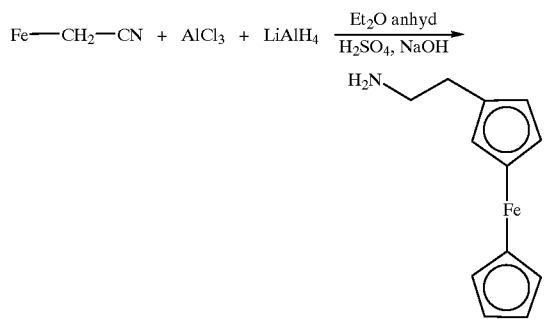

Method 1.36 g of AlCl$_3$ in 12 ml of anhydrous Et$_2$O is put into a three necked flask. 0.388 g of LiAlH$_4$ is added slowly. Once the addition is complete, 1.36 g of ferrocene-1-cyanomethyl (diluted in 12 ml of anhydrous (Et$_2$O) is added. The solution is stirred for 2½ hours under reflux.

Then the reaction medium is acidified with 15 ml of 6N sulphuric acid. The two phases are separated and the aqueous phase is washed with anhydrous Et$_2$O. The product is then in the NH$_3^+$ form and is therefore to be found in the aqueous phase. KOH is added until the pH=9. The product is then in the NH$_2$ form and therefore in the organic phase and is recovered, dried over potassium carbonate and evaporated.

0.45 g of a viscous orange liquid is obtained representing a yield of 15%.

2) NHP-ferrocene ethylamine coupling

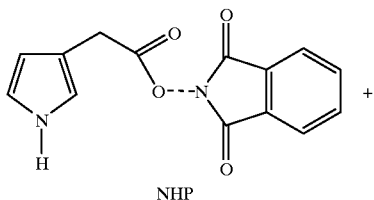

Method 160 g of NHP-pyrrole, 150 mg of ferrocene ethylamine and 10 ml of CH$_3$CN are mixed in a three necked flask. The solution is stirred for 48 hours. The CH$_3$CN is evaporated and the residue is dissolved in CHCl$_3$. The solution is washed twice with a 10% solution of NaHCO$_3$ then with water until pH7 is obtained. The organic phase is dried over MgSO$_4$ and the NaHCO$_3$ is evaporated.

120 mg of product are obtained representing a yield of 60%.

Example 9

Synthesis of Preferred Polymer (D)

1) Synthesis of 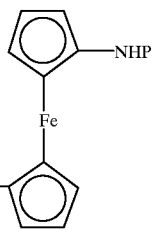

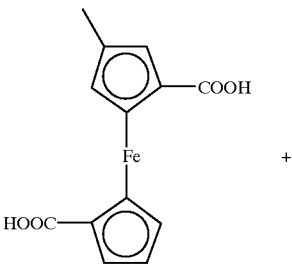

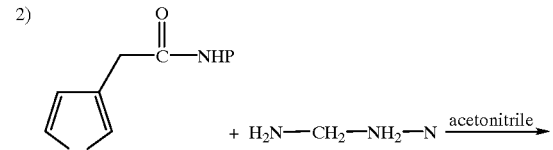
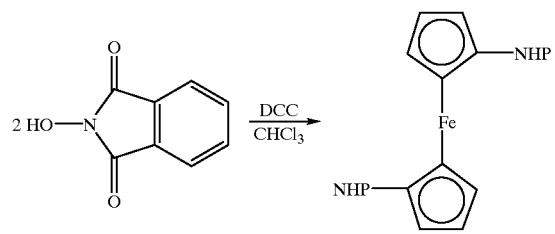
2) Coupling
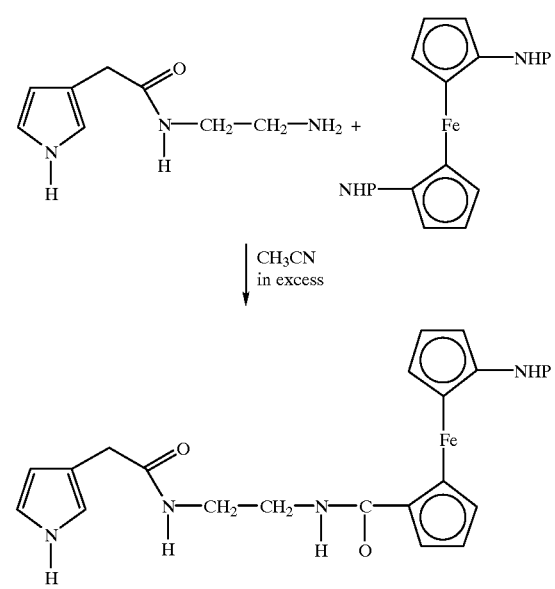
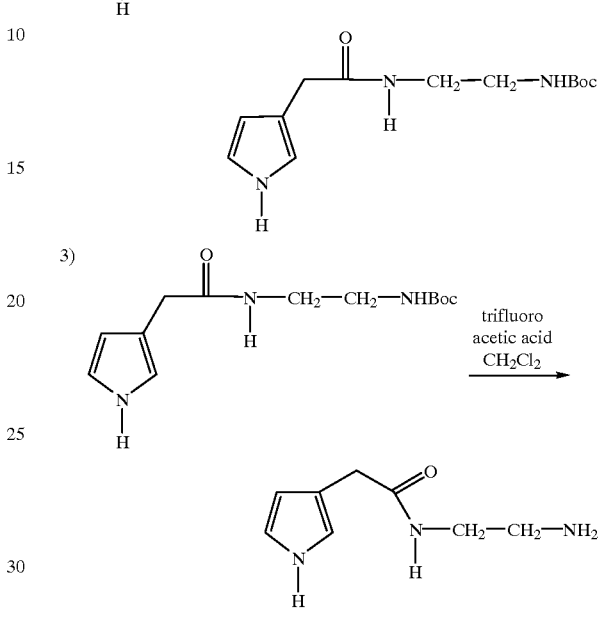
Example 11
Synthesis of Preferred Polymer (F)
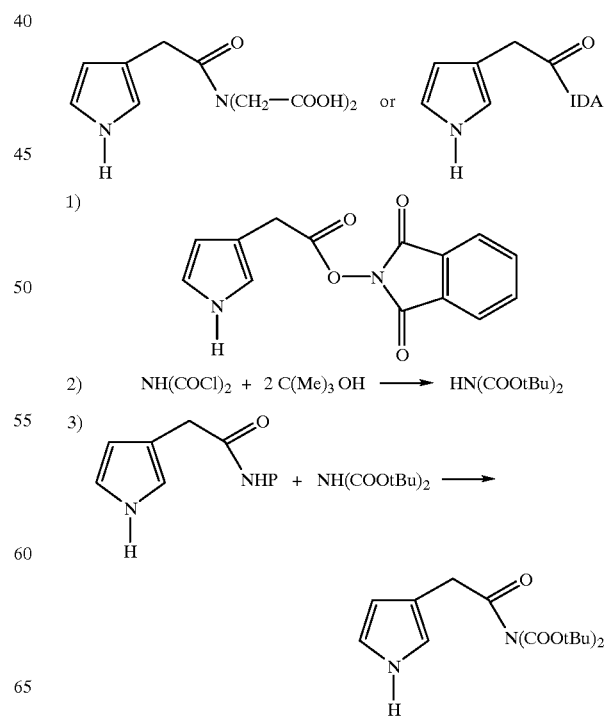
Example 10
Synthesis of Preferred Polymer (E)
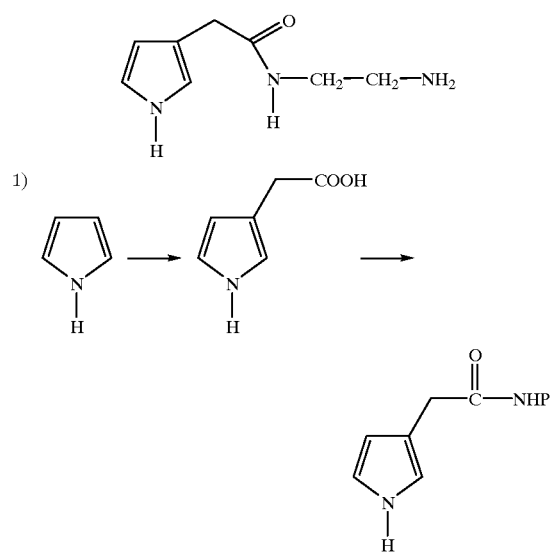

-continued

4) 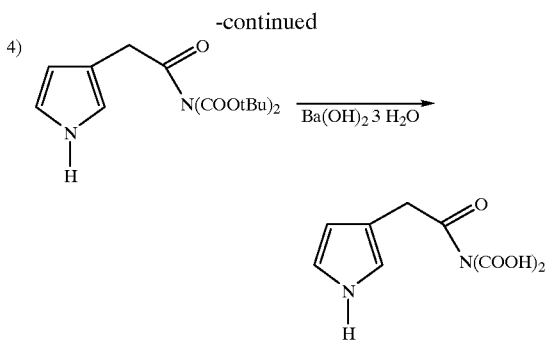

Example 12

Electropolymerisation

Homo- and co-polymers are obtained by electropolymerisation of corresponding monomers or monomer mixtures, the following conditions:
- solvent: acetonitrile or propylene carbonate
- electrolyte: $LiClO_4$ 0.1M
- potential: 0.9 V/SCE
- or current: 2–5 mA.cm$^{-2}$
- or potential scanning between 0–0.9 V/SCE
- electrode: Pt, Ag, Pd, $SnO_2$, Fe, Al
- concentration of monomer(s): $10^{-1}–2.10^{-1}$ M.l$^{-1}$

What is claimed is:

1. An electrically conductive, electroactive functionalized conjugated polymer of formula (I')

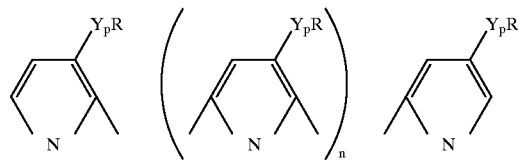

wherein
n is an integer or zero,
each R, which may be identical or different from one monomer unit to one another, is selected from the group consisting of H and functional groups capable of covalently bonding with a first biological molecule or antiligand with the proviso that (a) at least one said R of formula (I') represents said functional group or (b) if each $Y_pR$ in formula (I') is identical, they are different from $CH_2$—COOH,
each $Y_p$, which may be identical or different from one monomer unit to one another, is a coupling arm wherein p is zero or an integer,
wherein said polymer has a conductivity and an electroactivity which are substantially of the same order as a conductivity and an electroactivity of a corresponding polymer of formula (I'), in which each said R represents H.

2. The polymer of claim 1, wherein R is selected from the group consisting of COX, where X represents H, OH, a substituted or unsubstituted lower O-alkyl radical or an halogen; activated esters; NHZ where Z represents H, an alkyl radical or CO—$CF_3$; Si(alkyl)$_3$; Si(Alkoxyl)$_3$; electrochemical probes; electrochemical probes bound to an activated ester.

3. The polymer of claim 2, wherein the electrochemical probes are selected from the group consisting of ferrocene and quinone.

4. The polymer of claim 2, wherein activated esters are selected from the group consisting of COON-hydroxysuccinimide, COON-hydroxyphtalimide, and COO-pentafluorophenol.

5. The polymer of claim 1, wherein p is at least one and R is selected from the group consisting of H, OH, a substituted lower O-alkyl radical, and a halogen.

6. The polymer of claim 1, wherein Y is selected from the group consisting of alkylene groups having from 1 to 5 carbon atoms; oxy-alkylene groups having from 1 to 5 carbon atoms; polyethers having the formula [($CH_2$—$CH_2$—O)$_m$ ($CH_2$)$_{m'}$] where m is an integer ranging from 1 to 3 and m' is an integer equal to 1 or 2; ($CH_2$)$_m$ CONH ($CH_2$)$_{m''}$ where each of m and m" identical or different is an integer ranging from 1 to 3; ($CH_2$)$_m$ CON ($CH_2$)$_{m'''}$ where m is an integer ranging from 1 to 3 and m'" is 2 or 3.

7. The polymer of claim 1, wherein p is 0, 1 or 2.

8. The polymer of claim 2, wherein the halogen is chlorine.

9. The polymer of claim 1, wherein said antiligand is able to form an antiligand/target molecule complex.

10. The polymer of claim 9, wherein said complex is selected from the group consisting of peptide/antibody, antibody/haptene, hormone/receptor, polynucleotide hybrids/polynucleotide and polynucleotide/nucleic acid couple.

11. The polymer of claim 9, wherein the target molecule comprises a histidine tag.

12. The polymer of claim 1, wherein p is 1, Y is selected from the group consisting of $CH_2$, $CH_2$—$CH_2$ and $CH_2$—$CH_2$—$CH_2$, and at least one said R is COOH.

13. The polymer of claim 1, wherein p is 1, Y is selected from the group consisting of $CH_2$, $CH_2$—$CH_2$ and $CH_2$—$CH_2$—$CH_2$, and at least one said R is an activated ester.

14. The polymer of claim 13, wherein the activated ester is selected from the group consisting of COON-hydroxysuccinimide, COON-hydroxyphtalimide, and COO-pentafluorophenol.

15. The polymer of claim 1, wherein p is 1, Y is ($CH_2$)$_m$ CONH ($CH_2$)$_{m''}$ where each of m and m" identical or different is an integer ranging from 1 to 3, and at least one said R is an electrochemical probe.

16. The polymer of claim 15, wherein said electrochemical probe is selected from the group consisting of ferrocene and quinone.

17. The polymer of claim 15, wherein said electrochemical probe is bound to an activated ester.

18. The polymer of claim 1, wherein p is 1, Y is ($CH_2$)$_m$ CONH ($CH_2$)$_{m''}$ where each of m and m" identical or different is an integer ranging from 1 to 3, and at least one said R is $NH_2$ or any substituent possessing a terminal amino function $NH_2$.

19. The polymer of claim 1, wherein p is 1, Y is ($CH_2$)$_m$ CON ($CH_2$)$_{m'''}$ where m is an integer ranging from 1 to 3 and m'" is 2 or 3, and at least one R is COOH.

20. An electrically conductive, electroactive conjugated polymer of formula (II')

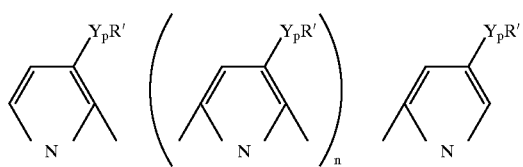

wherein n is an integer or zero, each R, which may be identical or different from one monomer unit to one another, is selected from the group consisting of H and functional groups capable of covalently bonding with, or covalently bonded to, a first biological molecule or antiligand with the proviso that at least one said R' of formula (II') represents one said functional group covalently bounded to one said first biological molecule or antiligand, each $Y_p$, which may be identical or different from one monomer unit to one another, is a coupling arm wherein p is zero or an integer, wherein said first biological molecule comprises a polynucleotide or peptide sequence.

21. The polymer of claim 20, wherein p in1, Y is selected from the group consisting of $CH_2$, $CH_2$—$CH_2$ and $CH_2$—$CH_2$—$CH_2$, and at least one said functional group, before being bonded to a first biological molecule or antiligand, is COOH.

22. The polymer of claim 20, wherein p is 1, Y is selected from the group consisting of $CH_2$, $CH_2$—$CH_2$ and $CH_2$—$CH_2$—$CH_2$, and at least one said functional group, before being bonded to a first biological molecule or antiligand, is an activated ester.

23. The polymer of claim 22, wherein the activated ester is selected from the group consisting of COON-hydroxysuccinimide, COON-hydroxyphtalimide, and COO-pentafluorophenol.

24. The polymer of claim 20, wherein p is 1, Y is $(CH_2)_m$ CONH $(CH_2)_{m''}$ where each of m and m" identical or different is an integer ranging from 1 to 3, and at least one said functional group, before being bonded to a first biological molecule or antiligand, is an electrochemical probe.

25. The polymer of claim 24, wherein the electrochemical probes are selected from the group consisting of ferrocene and quinone.

26. The polymer of claim 24, wherein said electrochemical probe is bound to an activated ester.

27. The polymer of claim 20, wherein p is 1, Y is $(CH_2)_m$ CONH $(CH_2)_{m''}$ where each of m and m" identical or different is an integer ranging from 1 to 3, and at least one said functional group, before being bonded to a first biological molecule or antiligand, is $NH_2$ or any substituent possessing a terminal amino function $NH_2$.

28. The polymer of claim 20, wherein p is 1, Y is $(CH_2)_m$ CON $(CH_2)_{m'''}$ where m is an integer ranging from 1 to 3 and m''' is 2 or 3, and at least one said functional group, before being bonded to a first biological molecule or antiligand, is COOH.

29. The polymer of claim 20, wherein the first biological molecule or antiligand is selected from the group consisting of amino acids, peptides, oligonucleotides, antigens.

* * * * *